US011090384B2

(12) United States Patent
Mahalingam et al.

(10) Patent No.: US 11,090,384 B2
(45) Date of Patent: Aug. 17, 2021

(54) ARTHROGENIC ALPHAVIRUS VACCINE

(71) Applicant: GRIFFITH UNIVERSITY, Brisbane (AU)

(72) Inventors: Surendran Mahalingam, Brisbane (AU); Adam Taylor, Brisbane (AU)

(73) Assignee: Griffith University, Nathan (AU)

( * ) Notice: Subject to any disclaimer, the term of this patent is extended or adjusted under 35 U.S.C. 154(b) by 0 days.

(21) Appl. No.: 16/304,509

(22) PCT Filed: May 25, 2017

(86) PCT No.: PCT/AU2017/050489
§ 371 (c)(1),
(2) Date: Nov. 26, 2018

(87) PCT Pub. No.: WO2017/201579
PCT Pub. Date: Nov. 30, 2017

(65) Prior Publication Data
US 2019/0134197 A1    May 9, 2019

(30) Foreign Application Priority Data

May 27, 2016   (AU) ............................... 2016902014
Feb. 13, 2017  (AU) ............................... 2017900446

(51) Int. Cl.
| A61K 39/12 | (2006.01) |
| A61P 31/14 | (2006.01) |
| C07K 14/005 | (2006.01) |
| C07K 19/00 | (2006.01) |
| C07K 7/00 | (2006.01) |
| G01N 33/569 | (2006.01) |
| A61K 39/42 | (2006.01) |
| C12N 7/00 | (2006.01) |
| A61K 39/00 | (2006.01) |

(52) U.S. Cl.
CPC .............. *A61K 39/42* (2013.01); *A61K 39/12* (2013.01); *A61P 31/14* (2018.01); *C07K 14/005* (2013.01); *C07K 19/00* (2013.01); *C12N 7/00* (2013.01); *G01N 33/56983* (2013.01); *A61K 2039/5254* (2013.01); *C07K 2319/09* (2013.01); *C12N 2770/36122* (2013.01); *C12N 2770/36134* (2013.01); *C12N 2770/36162* (2013.01); *G01N 2333/181* (2013.01); *Y02A 50/30* (2018.01)

(58) Field of Classification Search
None
See application file for complete search history.

(56) References Cited

U.S. PATENT DOCUMENTS

2014/0065178 A1\* 3/2014 Frolov ..................... C12N 7/00
424/186.1

FOREIGN PATENT DOCUMENTS

WO   WO 2012/106356   8/2012
WO   WO 2012/172574   12/2012

OTHER PUBLICATIONS

Lulla et al., Journal of Virology, 2013,87(22): 12003-12019. (Year: 2013).\*
Thomas et al., Virology Journal, 2013, 10:269. (Year: 2013).\*
GenBank Accession No. ADZ47899 (first available at NCBI on Mar. 19, 2011). (Year: 2011).\*
Akahata et al., "A virus-like particle vaccine for epidemic Chikungunya virus protects nonhuman primates against infection," Nature Medicine 16(3):334-339 (publication date: Mar. 2010, epublication date: Jan. 28, 2010).
Chu et al., "Deciphering the protective role of adaptive immunity to CHIKV/IRES a novel candidate vaccine against Chikungunya in the A129 mouse model," Vaccine 31:3353-3360 (publication date: Jul. 18, 2013, epublication date: May 29, 2013).
Favre et al., "Two nucleolar targeting signals present in the N-terminal part of Semliki Forest virus capsid protein," Archives of Virology 137(Issue 1-2):149-155 (publication Mar. 1994).
Fox et al., "Broadly Neutralizing Alphavirus Antibodies Bind an Epitope on E2 and Inhibit Entry and Egress," Cell 163(5):1095-1107 (publication date: Nov. 19, 2015, epublication date: Nov. 6, 2015).
Gérardin et al., "Chikungunya virus-associated encephalitis: A cohort study on La Réunion Island, 2005-2009," Neurology 86(1):94-102 (publication date: Jan. 5, 2016, epublication date: Nov. 25, 2015).
Goh et al., "Monoclonal antibodies specific for the capsid protein of chikungunya virus suitable for multiple applications," Journal of General Virology 96(Pt 3):507-512 (publication date: Mar. 2015, epublication date: Dec. 5, 2014).
Goh et al., "The Chikungunya Virus Capsid Protein Contains Linear B Cell Epitopes in the N- and C-Terminal Regions that are Dependent on an Intact C-Terminus for Antibody Recognition," Viruses 2943-2964 (publication date: Jun. 8, 2015).
Hoarau et al., "Persistent Chronic Inflammation and Infection by Chikungunya Arthritogenic Alphavirus in Spite of a Robust Host Immune Response," The Journal of Immunology 184:5914-5927 (publication date: May 15, 2010, epublication date: Apr. 19, 2010).
Labadie et al., "Chikungunya disease in nonhuman primates involves long-term viral persistence in macrophages," The Journal of Clinical Investigation 120(3):894-906 (publication date: Mar. 2010).
Muthumani et al., "Immunogenicity of novel consensus-based DNA vaccines against Chikungunya virus," Vaccine 26(40):5128-5134 (publication date: Sep. 19, 2008, epublication date: Apr. 14, 2008).

(Continued)

*Primary Examiner* — Nicole Kinsey White
(74) *Attorney, Agent, or Firm* — Perkins Coie LLP

(57) ABSTRACT

The invention relates to a vaccine comprising live attenuated recombinant alphavirus comprising mutated capsid protein. The invention also relates to a method of preventing a subject from contracting an alphaviral infection that would otherwise produce clinical signs of disease. In an embodiment the mutated capsid protein is Chikungunya virus (CHIKV) capsid protein having a mutated nucleolar localisation signal/sequence (NoLS), preferably the mutant NLS 101/95.

9 Claims, 17 Drawing Sheets
Specification includes a Sequence Listing.

(56) References Cited

OTHER PUBLICATIONS

Plante et al., "Novel Chikungunya Vaccine Candidate with an IRES-Based Attenuation and Host Range Alteration Mechanism," PLoS Pathogens 7(7):e1002142 (epublication date: Jul. 28, 2011).
Pohjala et al., "Inhibitors of alphavirus entry and replication identified with a stable Chikungunya replicon cell line and virus-based assays," PLoS One 6(12):e28923—(publication date: Dec. 19, 2011).
Roy et al., "A chimeric Sindbis-based vaccine protects cynomolgus macaques against a lethal aerosol challenge of eastern equine encephalitis virus," Vaccine 31:1464-1470 (publication date: Mar. 1, 2013, epublication date: Jan. 16, 2013).
Skoging-Nyberg et al., "M-X-I Motif of Semliki Forest Virus Capsid Protein Affects Nucleocapsid Assembly," Journal of Virology 75(10):4625-4632 (publication date: May 2001).
Taylor et al., "Mutation of the N-Terminal Region of Chikungunya Virus Capsid Protein: Implications for Vaccine Design," 8(1):e01970-16 (Jan./Feb. 2017).

* cited by examiner

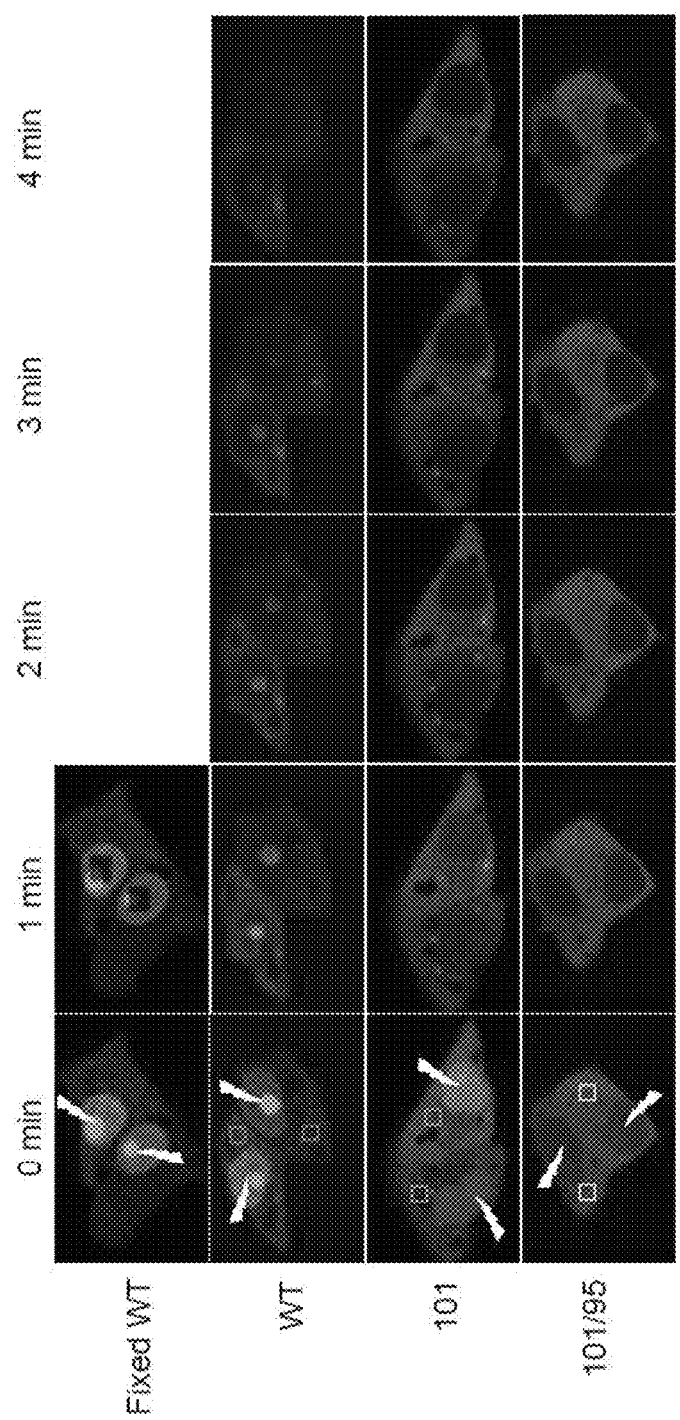
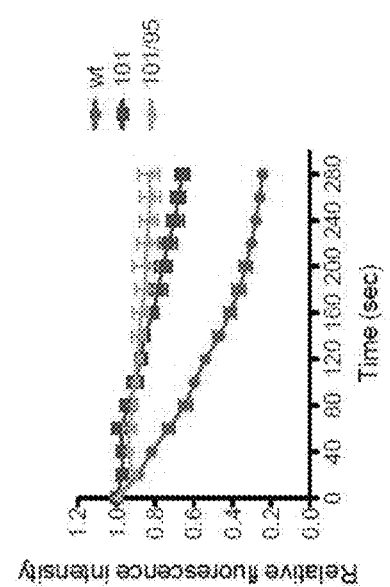
Figure 2(A)
Figure 2(B)

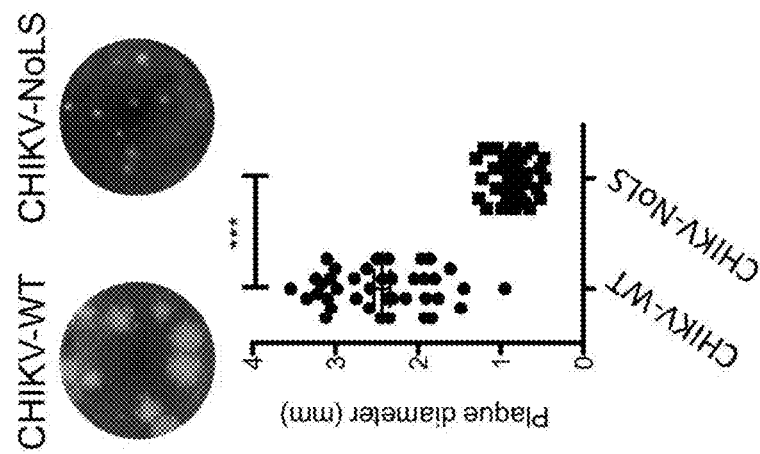
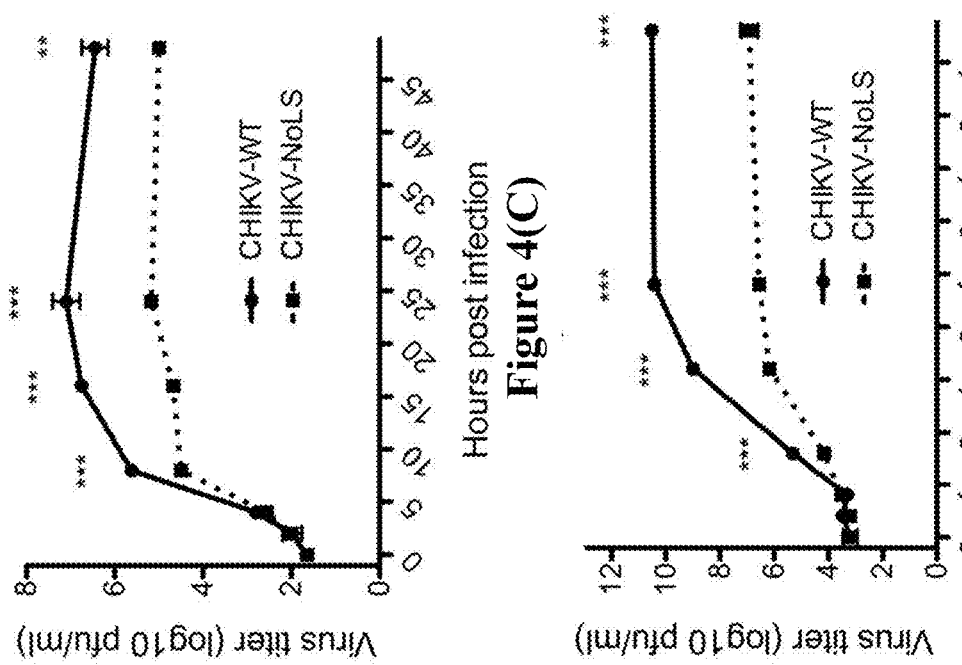
Figure 4(C) Figure 4(D) Figure 4(E)

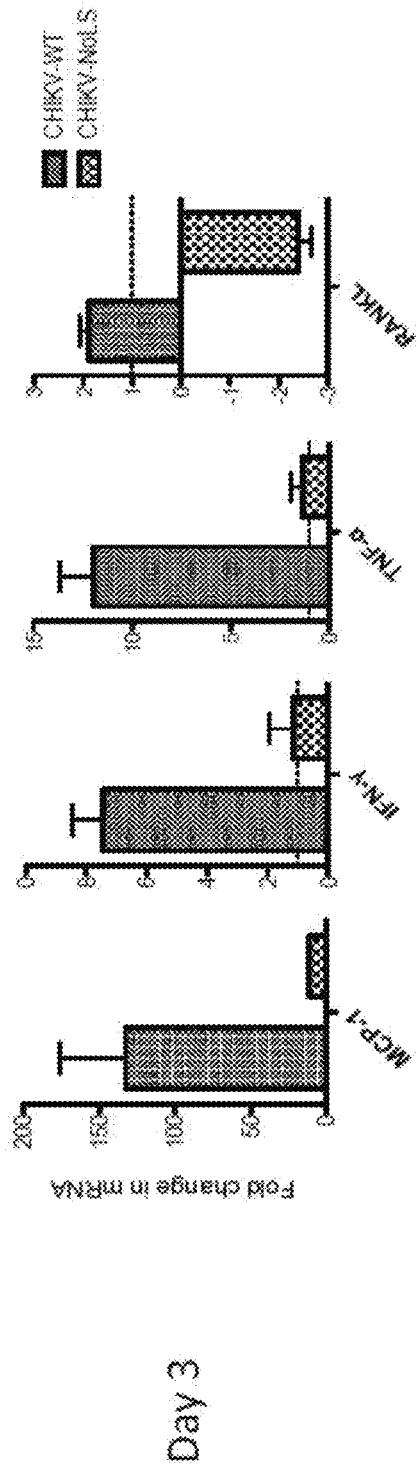
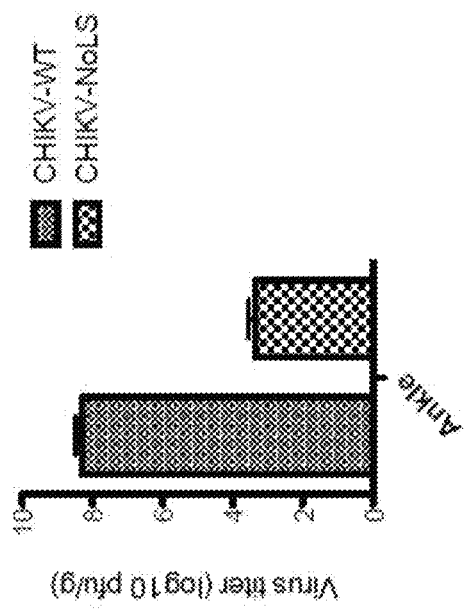
Figure 5(B)
Figure 5(A)

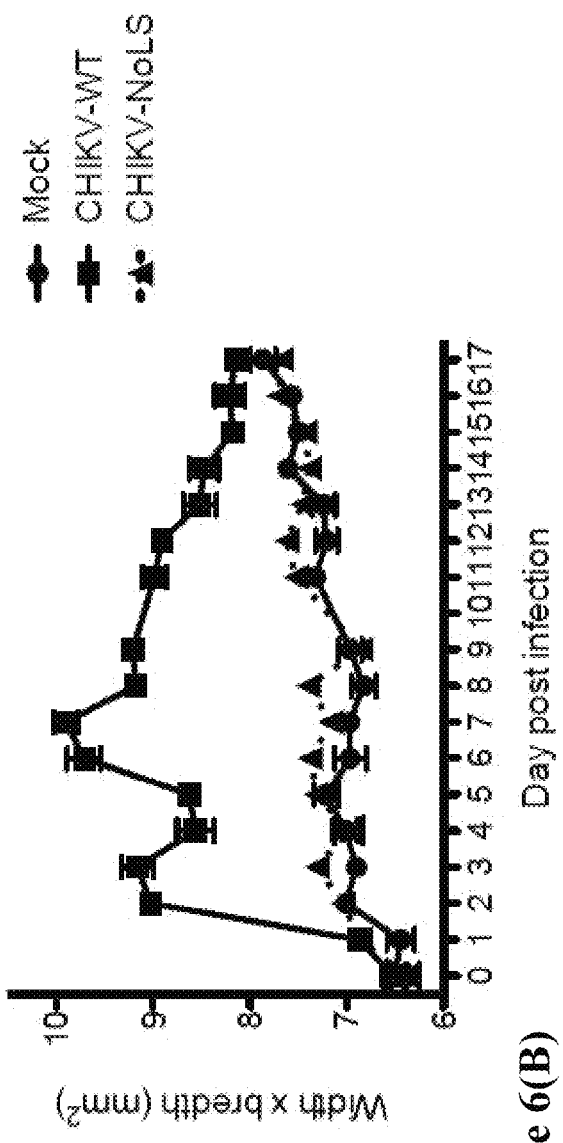
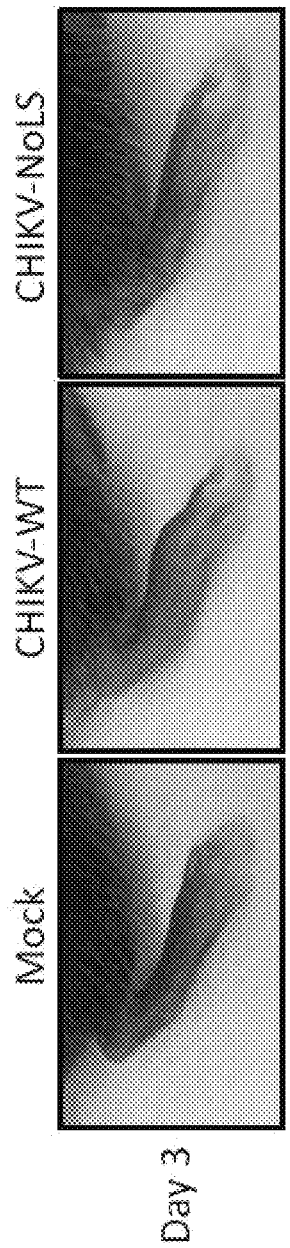
Figure 6(A)
Figure 6(B)

```
Chikv WT 1 MEFIPTQTFYNRRYQP----RPW--TPRPTIQVIRPRPRPQRQAGQLAQL   44
           |.:|||||||.||::|     |||  ...|...|:      |..||.|:.||
Sfv WT   1 MNYIPTQTFYGRRWRPRPAARPWPLQATPVAPVV-----PDFQAQQMQQL   45

Chikv   45 ISAVNKLTMR--AVPQQKPRRNRKNKKQKQKQQAPQNNTNQKKQPPKKKP   92
           |||||.||||  |:...:|.:.:|.|..|.|.:......|.|.|..|||.
Sfv     46 ISAVNALTMRQNAIAPARPPKPKKKKTTKPKPKTQPKKINGKTQQQKKKD   95

Chikv   93 AQ---KKKKPGRRERMCMKIENDCIFEVKHEGKVTGYACLVGDKVMKPAH  139
           .|   ||||||:||||||||||||||||||||||||||||||||||||||
Sfv     96 KQADKKKKKPGKRERMCMKIENDCIFEVKHEGKVTGYACLVGDKVMKPAH  145

Chikv  140 VKGTIDNADLAKLAFKRSSKYDLECAQIPVHMKSDASKFTHEKPEGYYNW  189
           |||.|||||||||||:||||||||||||||:|||||:||||||||:|||
Sfv    146 VKGVIDNADLAKLAFKKSSKYDLECAQIPVHMRSDASKYTHEKPEGHYNW  195

Chikv  190 HHGAVQYSGGRFTIPTGAGKPGDSGRPIFDNKGRVVAIVLGGANEGARTA  239
           |||||||||||||||||||||||||||||||||||||||||||||:|||
Sfv    196 HHGAVQYSGGRFTIPTGAGKPGDSGRPIFDNKGRVVAIVLGGANEGSRTA  245

Chikv  240 LSVVTWNKDIVTKITPEGAEEW [SEQ ID No. 1]
           ||||||||||:||::||||:|||
Sfv    246 LSVVTWNKDMVTRVTPEGSEEW [SEQ ID No. 2]
```

Figure 14

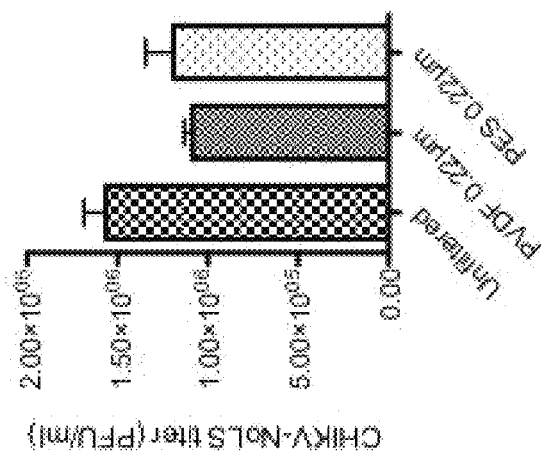
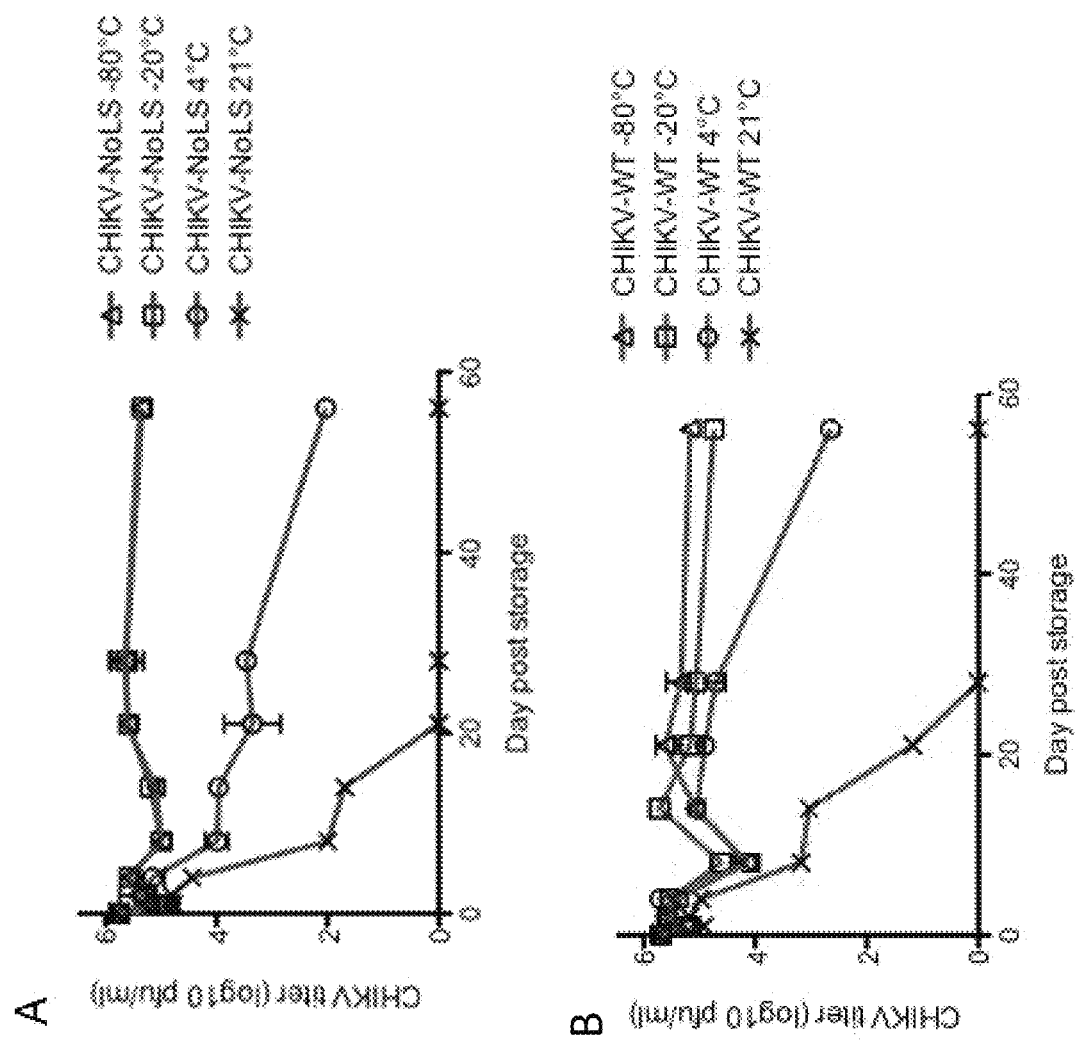
Figure 15
Figure 16

ARTHROGENIC ALPHAVIRUS VACCINE

TECHNICAL FIELD

The present invention relates to, inter alia, a vaccine comprising live attenuated recombinant alphavirus comprising mutated capsid protein. The present invention also relates to a method of preventing a subject from contracting an alphaviral infection that would otherwise produce clinical signs of disease. In a preferred embodiment the mutated capsid protein is Chikungunya virus (CHIKV) capsid protein having a mutated nucleolar localisation signal/sequence (NoLS).

BACKGROUND ART

Chikungunya virus (CHIKV) is a mosquito-borne, positive-sense single-stranded RNA virus and member of the Semliki Forest virus serogroup and genus Alphavirus. This group includes other alphaviruses that cause polyarthralgia and human joint disorders such as Ross River virus (endemic in Australia and the Pacific), O'nyong-nyong virus (Africa), Sindbis virus (SEW) (cause Pogosta disease [Finland], Ockeibo disease [Sweden] and Karelian fever [Russia]), Barmah Forest virus (Australia) and Mayaro virus (South and Central America). All of these viruses are transmitted by mosquitoes and have the ability to cause huge epidemics and emerge in new locations.

CHIKV replication takes place in the host cell cytoplasm. Upon entry into the cell, CHIKV particles undergo disassembly and the viral RNA genome is translated from two open reading frames to generate the non-structural and structural polyproteins. These polyproteins undergo cis and trans cleavage to form the mature viral proteins. Non-structural proteins largely form part of the replication complex, synthesising genomic and subgenomic RNA. Structural proteins package genomic RNA and, upon transit through the endoplasmic reticulum and golgi apparatus, are added to mature virions that bud from the cell containing a lipid bilayer.

Capsid protein is one of five structural proteins expressed from the subgenomic RNA of CHIKV and undergoes cis cleavage, via its serine protease activity, from the nascent structural polyprotein to form the mature viral protein. In a structural capacity, capsid protein recognises the packaging signals present in viral genomic RNA, allowing efficient assembly of the nucleocapsid core. The multifunctional capsid protein has a number of key roles in the alphavirus lifecycle.

The CHIKV capsid protein localises to the nucleolus of host cells. Semliki Forest virus (SFV) capsid protein is the only other alphavirus capsid protein reported to localise to the nucleolus of host cells. [Favre D1, Studer E, Michel M R. Arch Virol. 1994; 137(1-2):149-55. Two nucleolar targeting signals present in the N-terminal part of Semliki Forest virus capsid protein]. Two nucleolar targeting signals have previously been identified in the N-terminal part of the SFV capsid protein.

In humans, CHIKV infection typically causes a sharp onset of crippling joint pains, severe fever and rash. Joint disease ranges from mild arthralgia to severe, debilitating arthritis, with redness, swelling and synovial effusions. Although CHIKV disease is usually self-limiting and rarely fatal, the arthralgia is extremely painful and debilitating, typically lasting for 1 week but often much longer. Chronic arthralgia/arthritis frequently occurs after recovery from acute infection and is associated with persistence of viral RNA and protein in synovial macrophages and muscle [Hoarau J, et al. Persistent chronic inflammation and infection by chikungunya arthritogenic alphavirus in spite of a robust host immune response. J Immunol 2010 184:5914.27. Labadie K, et al. Chikungunya disease in nonhuman primates involves long-term viral persistence in macrophages. J Clin Invest. 2010 120:894]. Both the acute arthralgia and the chronic disease result in major losses in productivity. The very high (up to 50% of the population) and fast (45,000 cases in 1 week) attack rates for CHIKV, the chronic arthropathy, and the occasional severe clinical manifestations and mortality (infants and the elderly), cause a considerable economic and social burden. During major outbreaks CHIKV has also been shown to be a significant cause of CNS disease, particularly in infants and the elderly, with a case-fatality rate of CHIKV-associated encephalitis estimated to be 16.6% [Gérardin P, Couderc T, Bintner M et al. Chikungunya virus-associated encephalitis: A cohort study on La Réunion Island, 2005-2009. Neurology. 10.1212/WNL.0000000000002234. (2015)]. CHIKV is now a global problem, with outbreaks reported on most continents. Most recently CHIKV spread to the Americas affecting 43 countries and causing over 2 million cases of CHIKV disease between 2013-2015.

Currently there are no antivirals or commercially available vaccines to prevent CHIKV disease.

As mentioned, the Semliki Forest virus (SFV) serogroup includes other alphaviruses that are closely related to CHIKV, causing polyarthralgia and human joint disorders. These include, but are not limited to, Ross River virus (RRV), O'nyong-nyong virus (ONNV), Sindbis virus (SINV) (cause Pogosta disease, Ockelbo disease and Karelian fever), Barmah Forest virus (BFV) and Mayaro virus (MAYV). A growing body of evidence indicates cross-reactivity of alphavirus antibodies with broadly neutralising effects both in vitro and in vivo.

A number of strategies are currently being used to design a CHIKV-specific vaccine. These include chimeric live vaccines, which are highly attenuated and immunogenic in mice [Wang E, Kim D Y, Weaver S C, Frolov I. Chimeric Chikungunya viruses are nonpathogenic in highly sensitive mouse models but efficiently induce a protective immune response. J. Virol. 85(17), 9249-9252 (2011). Plante K, Wang E, Partidos C D et al. Novel chikungunya vaccine candidate with an IRES-based attenuation and host range alteration mechanism. PLoS Pathog. 7(7), e1002142 (2011)], virus-like particle based vaccines, which protected monkeys against viremia after challenge [Kahata W, Yang Z Y, Andersen H et al. A virus-like particle vaccine for epidemic chikungunya virus protects nonhuman primates against infection. Nat. Med. 16(3), 334-338 (2010)], and DNA vaccine design based on consensus envelope protein sequences [Muthumani K, Lankaraman K M, Laddy D J et al. Immunogenicity of novel consensus-based DNA vaccines against chikungunya virus. Vaccine 26(40), 5128-5134 (2008)].

Unlike a live-attenuated vaccine, some of these vaccine strategies will require multiple immunizations and will be expensive to manufacture.

SUMMARY OF INVENTION

Described herein is, inter alia, a vaccine comprising live attenuated recombinant alphavirus comprising mutated capsid protein.

According to a 1$^{st}$ form of the present invention, there is provided an isolated, purified, synthetic or recombinant alphaviral mutated capsid protein or a mutated nucleolar localisation region/signal/sequence (NoLS) thereof.

According to a 2$^{nd}$ form of the present invention, there is provided an isolated, purified, synthetic or recombinant alphaviral nascent structural polyprotein comprising a mutated capsid protein or a mutated nucleolar localisation region/signal/sequence (NoLS) thereof.

According to a 3$^{rd}$ form of the present invention, there is provided a recombinant alphaviral genome encoding a mutated capsid protein or a mutated nucleolar localisation region/signal/sequence (NoLS) thereof.

According to a 4$^{th}$ form of the present invention, there is provided a recombinant alphavirus comprising mutated capsid protein or a mutated nucleolar localisation region/signal/sequence (NoLS) thereof.

According to a 5$^{th}$ form of the present invention, there is provided a live attenuated recombinant alphavirus comprising mutated capsid protein or a mutated nucleolar localisation region/signal/sequence (NoLS) thereof.

According to a 6$^{th}$ form of the present invention, there is provided a chimeric alphavirus comprising mutated capsid protein or a mutated nucleolar localisation region/signal/sequence (NoLS) thereof.

According to a 7$^{th}$ form of the present invention, there is provided a live attenuated chimeric alphavirus comprising mutated capsid protein or a mutated nucleolar localisation region/signal/sequence (NoLS) thereof.

According to an 8$^{th}$ form of the present invention, there is provided a vaccine comprising:

an isolated, purified, synthetic or recombinant alphaviral mutated capsid protein or a mutated nucleolar localisation region/signal/sequence (NoLS) thereof;

an isolated, purified, synthetic or recombinant alphaviral nascent structural polyprotein comprising a mutated capsid protein or a mutated nucleolar localisation region/signal/sequence (NoLS) thereof;

a recombinant alphaviral genome encoding a mutated capsid protein or a mutated nucleolar localisation region/signal/sequence (NoLS) thereof;

a recombinant alphavirus comprising mutated capsid protein or a mutated nucleolar localisation region/signal/sequence (NoLS) thereof;

a live attenuated recombinant alphavirus comprising mutated capsid protein or a mutated nucleolar localisation region/signal/sequence (NoLS) thereof;

a chimeric alphavirus comprising mutated capsid protein or a mutated nucleolar localisation region/signal/sequence (NoLS) thereof; or a live attenuated chimeric alphavirus comprising mutated capsid protein or a mutated nucleolar localisation region/signal/sequence (NoLS) thereof.

According to a 9$^{th}$ form of the present invention, there is provided a sub-unit vaccine comprising: recombinant alphavirus comprising mutated capsid protein or a mutated nucleolar localisation region/signal/sequence (NoLS) thereof, recombinant alphaviral nascent structural polyprotein comprising a mutated capsid protein or a mutated nucleolar localisation region/signal/sequence (NoLS) thereof, or recombinant alphaviral genome encoding a mutated capsid protein or a mutated nucleolar localisation region/signal/sequence (NoLS) thereof.

According to a 10$^{th}$ form of the present invention, there is provided a serum containing alphavirus-neutralising antibodies obtained from a subject immunised with or administered the vaccine of the 8$^{th}$ form of the invention or the 9$^{th}$ form of the invention, the protein of the Pt form of the invention, the polyprotein of the 2$^{nd}$ form of the invention, the genome of the 3$^{rd}$ form of the invention, or the alphavirus of any one of the 4$^{th}$ to 7$^{th}$ forms of the invention.

According to an 11$^{th}$ form of the present invention, there is provided at least one alphavirus-neutralising antibody obtained from a subject immunised with the vaccine of the 8$^{th}$ form of the invention or the 9$^{th}$ form of the invention, the protein of the Pt form of the invention, the polyprotein of the 2$^{nd}$ form of the invention, the genome of the 3$^{rd}$ form of the invention, or the alphavirus of any one of the 4$^{th}$ to 7$^{th}$ forms of the invention.

According to a 12$^{th}$ form of the present invention, there is provided a pharmaceutical preparation comprising: (1) the protein of the Pt form of the invention or a pharmaceutically acceptable derivative thereof; (2) the polyprotein of the 2$^{nd}$ form of the invention or a pharmaceutically acceptable derivative thereof; (3) the genome of the 3$^{rd}$ form of the invention or a pharmaceutically acceptable derivative thereof; (4) the alphavirus of any one of the 4$^{th}$ to 7$^{th}$ forms of the invention or a pharmaceutically acceptable derivative thereof; (5) the vaccine of the 8$^{th}$ or 9$^{th}$ form of the invention or a pharmaceutically acceptable derivative thereof; (6) the serum of the 10$^{th}$ form of the invention or a pharmaceutically acceptable derivative thereof; or (7) the least one alphavirus-neutralising antibody of the 11$^{th}$ form of the invention or a pharmaceutically acceptable derivative thereof, and at least one pharmaceutically acceptable carrier.

According to a 13$^{th}$ form of the present invention, there is provided an immunogenic composition comprising: (1) the protein of the 1$^{st}$ form of the invention; (2) the polyprotein of the 2$^{nd}$ form of the invention; (3) the genome of the 3$^{rd}$ form of the invention; (4) the alphavirus of any one of the 4$^{th}$ to 7$^{th}$ forms of the invention; (5) the vaccine of the 8$^{th}$ or 9$^{th}$ form of the invention; (6) the serum of the 10$^{th}$ form of the invention; or (7) the least one alphavirus-neutralising antibody of the 11$^{th}$ form of the invention.

According to a 14$^{th}$ form of the present invention, there is provided a method of (1) preventing a subject from contracting an alphaviral infection naturally; (2) preventing a subject from developing alphaviral disease; (3) eliciting an alphaviral-protective immune response in a subject; or (4) stimulating an anti-alphaviral immune response in a subject, said method comprising the step of administering to the subject: (1) the protein of the 1$^{st}$ form of the invention; (2) the polyprotein of the 2$^{nd}$ form of the invention; (3) the genome of the 3$^{rd}$ form of the invention; (4) the alphavirus of any one of the 4$^{th}$ to 7$^{th}$ forms of the invention; or (5) the vaccine of the 8$^{th}$ or 9$^{th}$ form of the invention. Alternatively, there is provided use of (1) the protein of the 1$^{st}$ form of the invention; (2) the polyprotein of the 2$^{nd}$ form of the invention; (3) the genome of the 3$^{rd}$ form of the invention; (4) the alphavirus of any one of the 4$^{th}$ to 7$^{th}$ forms of the invention; or (5) the vaccine of the 8$^{th}$ or 9$^{th}$ form of the invention (in the preparation of a medicament) for (1) preventing a subject from contracting an alphaviral infection naturally; (2) preventing a subject from developing alphaviral disease; (3) eliciting an alphaviral-protective immune response in a subject; or (4) stimulating an anti-alphaviral immune response in a subject.

According to a 15$^{th}$ form of the present invention, there is provided a method of (1) treating a subject having alphaviral disease, or (2) reducing the severity of alphaviral disease, said method comprising the step of administering to the subject: (1) the serum of the 10$^{th}$ form of the invention or a pharmaceutically acceptable derivative thereof; or (2) the least one alphavirus-neutralising antibody of the 11$^{th}$ form of the invention or a pharmaceutically acceptable derivative thereof. Alternatively, there is provided use of (1) the serum of the 10th form of the invention or a pharmaceutically acceptable derivative thereof, or (2) the least one alphavirus-neutralising antibody of the 11th form of the invention or a pharmaceutically acceptable derivative thereof (in the preparation of a medicament) for (1) treating a subject having alphaviral disease, or (2) reducing the severity of alphaviral disease.

According to a 16th form of the present invention, there is provided a method of screening or diagnosing whether a subject has an alphaviral infection or disease, said method comprising the step of: (1) testing the subject, or biological sample obtained from the subject, for reactivity with the serum of the 10th form of the invention or the at least one alphavirus-neutralising antibody of the 11th form of the invention, wherein reactivity indicates that the subject has an alphaviral infection or disease; and, optionally: (2) treating the subject.

According to a 17th form of the present invention, there is provided an isolated, purified, synthetic or recombinant nucleic acid encoding the alphavirus capsid protein according to the 1st form of the invention or the polypeptide according to the 2nd form of the invention.

According to an 18th form of the present invention, there is provided an isolated, purified, synthetic or recombinant alphaviral genome encoding a mutated capsid protein.

According to a 19th form of the present invention, there is provided a vector comprising the nucleic acid according to the 17th form of the invention or the genome according to the 18th form of the invention.

According to a 20th form of the present invention, there is provided a cell comprising said vector according to the 19th form of the invention.

According to a 21st form of the present invention, there is provided a kit for carrying out the method according to any one of the 14th to 16th forms of the invention.

According to a 22nd form of the present invention, there is provided a method of preparing (1) the vaccine of the 8th or 9th form of the invention, or (2) the recombinant alphavirus of any one of 4th to 7th forms of the invention, said method comprising the steps of: (1) mutating a capsid protein of an alphavirus to produce a recombinant alphavirus; and (2) enabling the recombinant alphavirus to replicate.

Preferred features, embodiments and variations of the invention may be discerned from the following Detailed Description which provides sufficient information for those skilled in the art to perform the invention. The Detailed Description is not to be regarded as limiting the scope of the preceding Summary of Invention in any way.

The reference to any prior art in this specification is not, and should not be taken as an acknowledgement or any form of suggestion that the prior art forms part of the common general knowledge.

DETAILED DESCRIPTION

The present inventors have primarily developed a live-attenuated recombinant chikungunya virus (CHIKV) vaccine having a mutated capsid protein. The inventors have identified amino acids within the CHIKV wildtype capsid protein of importance for nucleolar localisation and viral replication, which they then mutated to produce a preferred form of the recombinant vaccine. In a disease model of CHIKV, mice infected with the recombinant vaccine/mutant CHIKV showed no signs of disease, significantly reduced virus titres and reduction in the levels of pro-inflammatory mediators versus wildtype CHIKV-infected mice. Mutant CHIKV infected mice challenged with wildtype CHIKV showed no sign of disease and significantly reduced viraemia versus mock infected mice challenged with wildtype CHIKV. Serum recovered from mutant CHIKV-infected mice was able to neutralise CHIKV infectivity in vitro 30 days post infection. With cross reactivity of neutralising antibodies acting between close members of the alphavirus family, the recombinant vaccine can also potentially act as a vaccine for other arthritogenic alphaviruses, such as Ross River virus (RRV), Barmah Forest virus (BFV), O'nyong-nyong virus (ONNV), Mayaro virus (MAYV), Sindbis virus group (causing Pogosta disease, Ockelbo disease and Karelian fever), and Semliki Forest virus (SFV). Similarly, it is thought that a mutated capsid protein from a closely related alphavirus other than CHIKV (such as from SFV) can be used in the development of a SFV-based live-attenuated recombinant vaccine. Moreover, a chimeric alphavirus containing a mutated capsid protein may offer much better vaccine protection, greater immunogenicity and/or neutralisation to the desired alphavirus, for not only arthritogenic alphaviruses but also encephalitic alphaviruses.

The mutated capsid protein can be developed based on any suitable type of alphavirus, including CHIKV, RRV, BFV, Sindbis virus group (causing Pogosta disease, Ockelbo disease and Karelian fever), SFV, ONNV and MAYV. In some embodiments, the mutated capsid protein can comprise a mutated nucleolar localisation region/signal/sequence (NoLS) compared with the wildtype capsid protein. For example, one or more polar (eg. serine, threonine, asparagine, glutamine, histidine and tyrosine) or charged amino acids (eg. lysine, arginine, aspartate and glutamate) can be shifted in position, deleted and/or exchanged for a hydrophobic amino acid (eg. alanine, valine, leucine, isoleucine, proline, phenylalanine, tryptophan, cysteine and methionine). For example, a charged amino acid can be replaced by a non-charged amino acid. In some embodiments, the mutated capsid protein can comprise one or more mutations other than in the NoLS. In some embodiments, the mutated capsid protein can comprise a mutated NoLS as well as one or more mutations other than in the NoLS. In some embodiments, the mutated capsid protein can comprise a mutated alphaviral NoLS fused to a different polypeptide, said different polypeptide having been derived from the same type of alphavirus or from a different type of alphavirus. For example, the different polypeptide can derive from a capsid protein from the same or different alphavirus. In other embodiments, the different protein may not be derived from an alphavirus. The mutated capsid protein is preferably a mutant of a wild-type capsid protein. Preferably the mutated capsid protein is based on CHIKV capsid protein [see SEQ. ID NO. 1].

In one embodiment the mutated capsid protein is incapable or substantially incapable of nucleolar localisation.

In another embodiment the mutated capsid protein enables assemblage of a nucleocapsid core of the recombinant alphavirus but substantially reduces the ability of the recombinant alphavirus to replicate.

In yet another embodiment the mutated capsid protein causes reduced or no clinical signs of alphavirus disease when administered to a subject.

In another embodiment the mutated capsid protein is incapable or substantially incapable of nucleolar localisation, the mutated capsid protein enables assemblage of a nucleocapsid core of the recombinant alphavirus but substantially reduces the ability of the recombinant alphavirus to replicate, and the mutated capsid protein causes reduced or no clinical signs of alphavirus disease when administered to a subject.

In another embodiment the mutated capsid protein causes a defect in infectious virus particle formation, causing reduction and delay of release of viral progeny.

The mutated capsid protein can have any suitable number of amino acid substitutions, additions and/or deletions differing from wild-type capsid protein, including one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or even more amino acid substitutions, additions and/or deletions. Preferably, the mutated capsid protein is a mutant of the wild-type CHIKV capsid protein. Examples are shown in FIG. 1 [SEQ. ID NOS. 4 to 7]. In some embodiments, one or more amino acids of the NoLS of wild-type CHIKV capsid protein can be shifted in position, replaced and/or deleted. In some embodiments, one or more of amino acid positions 58 to 110 of wild-type CHIKV capsid protein can be shifted in position, replaced and/or deleted. In some embodiments, one or more of amino acid positions 62, 63, 65, 66, 68, 69, 84, 85, 95, 96, 101 and 102 of wild-type CHIKV capsid protein can be shifted in position, replaced and/or deleted. In some embodiments, at least amino acid positions 62, 63, 65, 66, 68, 69, 84, 85, 95, 96, 101 and 102 of wild-type CHIKV capsid protein can be shifted in position, replaced and/or deleted.

In one embodiment, the mutated capsid protein is incapable or substantially incapable of nucleolar localisation by way of having at least one mutation in the nucleolar localisation region/signal/sequence (NoLS) compared with the wildtype capsid protein. By "at least one mutation" it is meant that the mutated capsid protein can have at least one amino acid substitution, addition and/or deletion, including one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or even more amino acid substitutions, additions and/or deletions. Examples are shown in FIG. 1 [SEQ. ID NOS. 4 to 7].

Preferably, the mutated capsid protein is a NoLS mutant of the wild-type CHIKV capsid protein. For example, one or more amino acids of the wild-type CHIKV capsid protein required for nucleolar localisation can be replaced by one or more other types of amino acids, or one or more of the amino acids required for nucleolar localisation may be deleted. Examples are shown in FIG. 1 [SEQ. ID NOS. 4 to 7].

In some embodiments, the mutated capsid protein can have one or more amino acid substitutions, additions and/or deletions present between residues 58 and 110 of wild type CHIKV capsid protein. Examples are shown in FIG. 1 [SEQ. ID NOS. 4 to 7].

In some embodiments, the mutated capsid protein can have one or more amino acid substitutions, additions and/or deletions between residues 66 to 83 and/or 92 to 105 of wild type Semliki Forest Virus capsid protein [see FIG. 11, SEQ. ID NO. 2].

In another embodiment, the mutated capsid protein may enable assemblage of a nucleocapsid core of the recombinant alphavirus but substantially reduce the ability of the recombinant alphavirus to replicate by way of having at least one mutation. Again, the mutated capsid protein can have at least one amino acid substitution, addition and/or deletion, including one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or even more amino acid substitutions, additions and/or deletions. Preferably, the mutated capsid protein is a mutant of the wild-type CHIKV capsid protein. For example, one or more amino acids of the wild-type CHIKV capsid protein can be replaced by one or more other types of amino acids, or one or more of the amino acids may be deleted. Examples are shown in FIG. 1 [SEQ. ID NOS. 4 to 7].

Suitable mutated capsid protein (partial) sequences having a mutated NoLS signal/sequence are shown in FIG. 1(A) and include mutants NLS 101/95 [SEQ. ID NO. 7] and NLS 101 [SEQ. ID NO. 6]. For the mutant NLS 101/95, positively charged amino acids required for nucleolar transportation have been replaced with alanine. For clarity, mutants NLS 101/95 and NLS 101 each have a protein sequence identical to the wild-type CHIKV capsid protein, except for the amino acid differences shown in FIG. 1(A).

The full wild-type sequence of CHIKV capsid protein can be found at www.ncbi.nlm.nih.gov/nuccore/KT449801.1 and is also shown in FIG. 11 [SEQ. ID NO. 1].

If it is found that mutation of the capsid NoLS signal/sequence does not offer a substantial level of attenuation, then one or more additional mutations (eg. amino acid substitution, insertion and/or deletion) which further attenuate the virus containing the NoLS mutation can be made. The one or more additional mutations (eg. amino acid substitution, insertion and/or deletion) can be made in the capsid protein or elsewhere in the genome of the alphavirus.

Likewise, suitable mutated capsid proteins can be developed from the capsid proteins of other alphaviruses, such as the capsid protein of SFV. FIG. 11 shows the NoLS region of the SFV wild-type capsid protein sequence [SEQ. ID NO. 2]. Mutations as described above for CHKV capsid protein may be made to the SFV wild-type capsid protein.

By "incapable or substantially incapable of nucleolar localisation" it is meant that the mutated capsid protein is substantially absent from the nucleolus. An example of this is mutant NLS 101/95 [see SEQ. ID NO. 7].

By "enables assemblage of a nucleocapsid core of the recombinant alphavirus but substantially reduces the ability of the recombinant alphavirus to replicate" it is meant that the ability of the recombinant alphavirus to replicate is significantly diminished, yet the alphavirus is still able to elicit an effective immune response. An example of this is mutant NLS 101/95 [see SEQ. ID NO. 7].

By "live attenuated" it is meant that the virus demonstrates substantially reduced or preferably no clinical signs of disease when administered to a subject.

The vaccine can comprise live virus or inactivated virus. If inactivated, it can be inactivated in any suitable way (e.g. using high or low temperatures, or chemically).

Preferably the vaccine provides long-lived immunity to the subject. For example, if vaccinated with mutant CHIKV capsid protein, then preferably the subject is provided with long-lived immunity to CHIKV disease.

Preferably the vaccine is able to protect against CHIKV isolates of differing genotypes (large number of isolates from different localities and regions).

The subject may also be provided with long-lived immunity to one or more other types of alphaviruses.

The vaccine, especially the live attenuated vaccine, may offer cross protection against other arthritogenic alphaviruses, such as CHIKV, RRV, BFV, Sindbis virus group (causing Pogosta disease Ockelbo disease and Karelian fever), SFV, MAYV or ONNV, which share a greater degree of structural and genetic homology to CHIKV. That is, a live attenuated vaccine based on CHKV mutant protein may offer cross protection against RRV, BFV, Sindbis virus group, SFV, MAYV and/or ONNV.

The chimeric alphavirus may be effective against encephalitic alphaviruses, such as Eastern equine encephalitis virus (EEEV) and Venezuelan equine encephalitis virus (VEEV), which are more distantly related. The chimeric alphavirus may comprise mutated capsid protein and all or part of the structural polyprotein or non-structural polyprotein of an encephalitic alphavirus. In an embodiment, the chimeric alphavirus comprises the mutant capsid protein of CHIKV or other closely related alphavirus and all or part of the structural polyprotein or non-structural polyprotein of an encephalitic alphavirus.

A chimeric alphavirus, containing the mutant NLS 101/95 capsid protein of CHIKV [see SEQ. ID NO. 7] and proteins of a desired alphavirus, may offer greater immunogenicity and/or neutralisation to the desired alphavirus.

The chimeric alphavirus can be prepared in any suitable way. Such techniques are described in the following reference: Roy C J, Adams A P, Wang E, Leal G, Seymour R L, Sivasubramani S K, Mega W, Frolov I, Didier P J, Weaver S C. Vaccine. 2013. A chimeric Sindbis-based vaccine protects cynomolgus macaques against a lethal aerosol challenge of eastern equine encephalitis virus.

The recombinant alphavirus comprising mutated capsid protein can be prepared in any suitable way. The vaccine comprising live attenuated recombinant alphavirus comprising mutated capsid protein can be of any suitable form and can be prepared in any suitable way. Similarly, live attenuated recombinant alphavirus comprising mutated capsid protein can be of any suitable form and can be prepared in any suitable way. Such techniques are described in the following reference, the entire contents of which are incorporated herein by way of cross-reference: Chu H, Das S C, Fuchs J F, Suresh M, Weaver S C, Stinchcomb D T, Partidos C D, Osorio J E. Deciphering the protective role of adaptive immunity to CHIKV/IRES a novel candidate vaccine against Chikungunya in the A129 mouse model. Vaccine. 2013 Jul. 18; 31(33):3353-60. doi: 10.1016/j.vaccine.2013.05.059. Epub 2013 May 29.

In some embodiments the vaccine can be prepared by way of passing recombinant alphavirus through a filter, such as a 0.22 μm hydrophilic PVDF membrane or hydrophilic Polyethersulfone membrane.

In some embodiments the vaccine can be stored long term and remain viable at a temperature of between about −20° C. and about −80° C. By "long-term" it is meant that the vaccine can remain viable for at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 days. In some embodiments it is possible that the vaccine can remain viable for more than 60 days.

The live attenuated recombinant alphavirus comprising mutated capsid protein can be in the form of an isolate. The isolate may comprise cells, such as mammalian, insect (eg. mosquito) or other types of cells.

The serum containing alphavirus-neutralising antibodies can be of any suitable form and can be prepared in any suitable way. The at least one alphavirus-neutralising antibody can be prepared in any suitable way. The antibody can be isolated, recombinant or purified. Preferably there are many alphavirus-neutralising antibodies. Such techniques are described in the following reference, the entire contents of which are incorporated herein by way of cross-reference: Fox J M, Long F, Edeling M A, Lin H, van Duijl-Richter M K, Fong R H, Kahle K M, Smit J M4, Jin J, Simmons G, Doranz B J, Crowe J E Jr, Fremont D H, Rossmann M G, Diamond M S. Broadly Neutralizing Alphavirus Antibodies Bind an Epitope on E2 and Inhibit Entry and Egress. Cell. 2015 Nov. 19; 163(5):1095-107. doi: 10.1016/j.cell.2015.10.050. Epub 2015 Nov. 6.

The pharmaceutical preparation can be prepared in any suitable way.

The method of preventing the subject from contracting an alphaviral infection, treating a subject having an alphaviral infection, or reducing the severity of an alphaviral infection, can be carried out in any suitable way.

The vaccine, live attenuated recombinant alphavirus, pharmaceutical preparation and immunogenic composition (described hereafter as "the compositions") can be administered independently, either systemically or locally, by any method standard in the art, for example, subcutaneously, intravenously, parenterally, intraperitoneally, intradermally, intramuscularly, topically, or nasally.

The compositions can comprise conventional non-toxic, physiologically or pharmaceutically acceptable ingredients or vehicles suitable for the method of administration and are well known to an individual having ordinary skill in this art. The compositions can, for example, comprise an adjuvant. The term "pharmaceutically acceptable carrier" as used herein is intended to include diluents such as saline and aqueous buffer solutions. The compositions can be in aqueous or lyophilized form.

A variety of devices are known in the art for delivery of the compositions including, but not limited to, syringe and needle injection, bifurcated needle administration, administration by intradermal patches or pumps, intradermal needle-free jet delivery (intradermal etc), intradermal particle delivery, or aerosol powder delivery.

The compositions can be administered independently one or more times to achieve, maintain or improve upon a desired effect/result. It is well within the skill of an artisan to determine dosage or whether a suitable dosage of the composition comprises a single administered dose or multiple administered doses. An appropriate dosage depends on the subject's health, the induction of immune response and/or prevention of infection caused by the alphavirus, the route of administration and the formulation used. For example, a therapeutically active amount of the compound may vary according to factors such as the disease state, age, sex, and weight of the subject, and the ability of the composition to elicit a desired response in the subject. Dosage regima may be adjusted to provide the optimum therapeutic response. For example, a subject may be administered a 'booster' vaccination one or two weeks following the initial administration.

The method of screening or diagnosing whether a subject has an alphaviral infection or disease can be carried out in any suitable way.

Some forms of the invention concern a biological sample or a step of isolating one or more biological samples from a subject. Typically, any form of the invention concerning testing of a subject etc. may involve the step of isolating one or more biological samples from the subject and testing that/those.

The biological sample can be any suitable sample derived from the subject—obtained either non-invasively or invasively. It can be cellular- or extracellular-derived, or both. For example: 1. Buccal (mouth) cells—obtained by swishing mouthwash in the mouth or by swabbing or brushing the inside of the cheek with a swab or brush; 2. Blood—obtained by pricking the finger and collecting the drops (dried blood spot) or by venepuncture (whole blood); 3. Skin—obtained by a (punch) biopsy; 4. Organ tissue— obtained by biopsy; 5. Plasma—obtained by blood plasma fractionation; 6. Urine—obtained by urination; 7. Faeces—obtained by stool sample; 8. Cerebrospinal fluid—obtained by spinal tap; and 9. Sputum—obtained by expectoration or nasotracheal suctioning.

Techniques for biological sample collection are well known to skilled persons.

The isolated, purified, synthetic or recombinant alphavirus capsid protein or polyprotein or genome can be prepared in any suitable way. The isolated, purified, synthetic or recombinant genome or nucleic acid encoding the alphavirus capsid protein can be prepared in any suitable way. The vector can also be prepared in any suitable way.

The cell (insect, mammalian or other) comprising the vector can be prepared in any suitable way.

The kit for carrying out the above mentioned methods can contain any suitable components or articles—eg. vaccine comprising live attenuated alphavirus, live attenuated recombinant alphavirus, pharmaceutical formulation etc; serum or one or more antibodies; one or more articles and/or reagents for performance of the method, such as means for providing the test sample itself; and, instructions.

Suitable protocols for carrying out one or more of the above-mentioned techniques can be found in "Current Protocols in Molecular Biology", July 2008, JOHN WILEY AND SONS; D. M. WEIR AND CC BLACKWELL, "Handbook Of Experimental Immunology", vol. I-IV, 1986; JOHN E. COLIGAN, ADA M. KRUISBEEK, DAVID H. MARGULIES, ETHAN M. SHEVACH, WARREN STROBER, "Current Protocols in Immunology", 2001, JOHN WILEY & SONS; "Immunochemical Methods In Cell And Molecular Biology", 1987, ACADEMIC PRESS; SAMBROOK ET AL., "Molecular Cloning: A Laboratory Manual, 3d ed.,", 2001, COLD SPRING HARBOR LABORATORY PRESS; "Vaccine Design, Methods and Protocols", Volume 2, Vaccines for Veterinary Diseases, Sunil Thomas in Methods in Molecular Biology (2016); and, "Vaccine Design, Methods and Protocols", Volume 1: Vaccines for Human Diseases, Sunil Thomas in Methods in Molecular Biology (2016), the entire contents of which are incorporated herein by way of cross-reference.

Any suitable type of subject can be used. The subject can be any suitable mammal. Mammals include humans, primates, livestock and farm animals (eg. horses, sheep and pigs), companion animals (eg. dogs and cats), and laboratory test animals (eg. rats, mice and rabbits). The subject is preferably human.

'Nucleic acid' as used herein includes 'polynucleotide', 'oligonucleotide', and 'nucleic acid molecule', and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide.

As used herein, the term 'recombinant' refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The terms 'isolated' or 'purified' as used herein mean essentially free of association with other biological components/contaminants, e.g., as a naturally occurring protein that has been separated from cellular and other contaminants by the use of antibodies or other methods or as a purification product of a recombinant host cell culture.

Any of the features described herein can be combined in any combination with any one or more of the other features described herein within the scope of the invention.

Unless defined otherwise, all technical and scientific terms used herein have the same meaning as commonly understood by one of ordinary skill in the art to which this invention belongs. Although any methods and materials similar or equivalent to those described herein can also be used in the practise or testing of the present invention.

In the present specification and claims (if any), the word 'comprising' and its derivatives including 'comprises' and 'comprise' include each of the stated integers but does not exclude the inclusion of one or more further integers.

Particularly preferred embodiments of the invention are defined below.

1. An isolated, purified, synthetic or recombinant Chikungunya virus (CHIKV) or Semliki Forest virus (SFV) alphaviral mutated capsid protein.

2. An isolated, purified, synthetic or recombinant CHKV or SFV alphaviral nascent structural polyprotein comprising a mutated capsid protein.

3. A recombinant CHKV or SFV alphaviral genome encoding a mutated capsid protein.

4. A recombinant CHKV or SFV alphavirus comprising mutated capsid protein.

5. A live attenuated recombinant CHKV or SFV alphavirus comprising mutated capsid protein.

6. A chimeric CHKV or SFV alphavirus comprising mutated capsid protein.

7. A live attenuated chimeric CHKV or SFV alphavirus comprising mutated capsid protein.

8. A vaccine comprising:
an isolated, purified, synthetic or recombinant CHKV or SFV alphaviral mutated capsid protein;
an isolated, purified, synthetic or recombinant CHKV or SFV alphaviral nascent structural polyprotein comprising a mutated capsid protein;
a recombinant CHKV or SFV alphaviral genome encoding a mutated capsid protein;
a recombinant CHKV or SFV alphavirus comprising mutated capsid protein;
a live attenuated recombinant CHKV or SFV alphavirus comprising mutated capsid protein;
a chimeric CHKV or SFV alphavirus comprising mutated capsid protein; or
a live attenuated chimeric CHKV or SFV alphavirus comprising mutated capsid protein.

9. A sub-unit vaccine comprising: recombinant CHKV or SFV alphavirus comprising mutated capsid protein; recombinant CHKV or SFV alphaviral nascent structural polyprotein comprising a mutated capsid protein; or recombinant CHKV or SFV alphaviral genome encoding a mutated capsid protein.

10. A serum containing alphavirus-neutralising antibodies obtained from a subject immunised with or administered the vaccine of paragraph 8 or paragraph 9, the protein of paragraph 1, the polyprotein of paragraph 2, the genome of paragraph 3, or the alphavirus of any one of paragraphs 4 to 7.

11. At least one alphavirus-neutralising antibody obtained from a subject immunised with or administered the vaccine of paragraph 8 or paragraph 9, the protein of paragraph 1, the polyprotein of paragraph 2, the genome of paragraph 3, or the alphavirus of any one of paragraphs 4 to 7.

12. A pharmaceutical preparation comprising: (1) the protein of paragraph 1 or a pharmaceutically acceptable derivative thereof; (2) the polyprotein of paragraph 2 or a pharmaceutically acceptable derivative thereof; (3) the genome of paragraph 3 or a pharmaceutically acceptable derivative thereof; (4) the alphavirus of any one of paragraphs 4 to 7 or a pharmaceutically acceptable derivative thereof; (5) the vaccine of paragraph 8 or paragraph 9 or a pharmaceutically acceptable derivative thereof; (6) the serum of paragraph 10 or a pharmaceutically acceptable derivative thereof; or (7) the least one alphavirus-neutralising antibody of paragraph 11 or a pharmaceutically acceptable derivative thereof, and at least one pharmaceutically acceptable carrier.

13. An immunogenic composition comprising: (1) the protein of paragraph 1; (2) the polyprotein of paragraph 2; (3) the genome of paragraph 3; (4) the alphavirus of any one of paragraphs 4 to 7; (5) the vaccine of paragraph 8 or paragraph 9; (6) the serum of paragraph 10; or (7) the least one alphavirus-neutralising antibody of paragraph 11.

14. A method of (1) preventing a subject from contracting an alphaviral infection naturally; (2) preventing a subject from developing alphaviral disease; (3) eliciting an alphaviral-protective immune response in a subject; or (4) stimulating an anti-alphaviral immune response in a subject, said method comprising the step of administering to the subject: (1) the protein of paragraph 1; (2) the polyprotein of paragraph 2; (3) the genome of paragraph 3; (4) the alphavirus of any one of paragraphs 4 to 7; or (5) the vaccine of paragraph 8 or paragraph 9.

15. A method of (1) treating a subject having alphaviral disease, or (2) reducing the severity of alphaviral disease, said method comprising the step of administering to the subject: (1) the serum of paragraph 10 or a pharmaceutically acceptable derivative thereof; or (2) the least one alphavirus-neutralising antibody of paragraph 11 or a pharmaceutically acceptable derivative thereof.

16. A method of screening or diagnosing whether a subject has an alphaviral infection or disease, said method comprising the step of: (1) testing the subject, or biological sample obtained from the subject, for reactivity with the serum of paragraph 10 or the at least one alphavirus-neutralising antibody of paragraph 11, wherein reactivity indicates that the subject has an alphaviral infection or disease; and, optionally: (2) treating the subject.

17. An isolated, purified, synthetic or recombinant nucleic acid encoding the alphavirus capsid protein of paragraph 1 or the polypeptide of paragraph 2.

18. An isolated, purified, synthetic or recombinant CHIKV or SFV alphaviral genome encoding a mutated capsid protein.

19. A vector comprising the nucleic acid of paragraph 17 or the genome of paragraph 18.

20. A cell comprising the vector of paragraph 19.

21. A kit for carrying out the method according to paragraph 14, 15 or 16.

22. A method of preparing (1) the vaccine of paragraph 8 or paragraph 9, or (2) the recombinant alphavirus of any one of paragraphs 4 to 7, said method comprising the steps of: (1) mutating a capsid protein of a CHICKV or SFV alphavirus to produce a recombinant alphavirus; and (2) enabling the recombinant alphavirus to replicate.

23. The protein of paragraph 1, the polyprotein of paragraph 2, the genome of paragraph 3, the alphavirus of any one of paragraphs 4 to 6, the vaccine of paragraph 8 or 9, the serum of paragraph 10, the at least one antibody of paragraph 11, the pharmaceutical preparation of paragraph 12, the immunogenic composition of paragraph 13, the method of any one of paragraphs 14 to 16, the nucleic acid of paragraph 17, the genome of paragraph 18, the vector of paragraph 19, the cell of paragraph 20, the kit of paragraph 21, or the method of paragraph 22, wherein the mutated capsid protein has: a mutated nucleolar localisation region/signal/sequence (NoLS) compared with the wildtype capsid protein; one or more mutations other than in the NoLS; a mutated NoLS as well as one or more mutations other than in the NoLS; one or more amino acids of the NoLS of wild-type CHIKV capsid protein shifted in position, replaced and/or deleted; one or more of amino acid positions 58 to 110 of wild-type CHIKV capsid protein shifted in position, replaced and/or deleted; one or more of amino acid positions 62, 63, 65, 66, 68, 69, 84, 85, 95, 96, 101 and 102 of wild-type CHIKV capsid protein shifted in position, replaced and/or deleted; at least amino acid positions 62, 63, 65, 66, 68, 69, 84, 85, 95, 96, 101 and 102 of wild-type CHIKV capsid protein shifted in position, replaced and/or deleted; or a sequence as shown or as substantially shown in any one of SEQ. ID NOS. 1 and 4 to 7.

24. The protein of paragraph 1, the polyprotein of paragraph 2, the genome of paragraph 3, the alphavirus of any one of paragraphs 4 to 6, the vaccine of paragraph 8 or 9, the serum of paragraph 10, the at least one antibody of paragraph 11, the pharmaceutical preparation of paragraph 12, the immunogenic composition of paragraph 13, the method of any one of paragraphs 14 to 16, the nucleic acid of paragraph 17, the genome of paragraph 18, the vector of paragraph 19, the cell of paragraph 20, the kit of paragraph 21, or the method of paragraph 22, wherein the mutated capsid protein is Capsid-101/95 (CHIKV-NoLS) [SEQ. ID NO. 7].

25. An isolated, purified, synthetic or recombinant alphaviral mutated capsid protein.

26. An isolated, purified, synthetic or recombinant alphaviral nascent structural polyprotein comprising a mutated capsid protein.

27. A recombinant alphaviral genome encoding a mutated capsid protein.

28. A recombinant alphavirus comprising mutated capsid protein.

29. A live attenuated recombinant alphavirus comprising mutated capsid protein.

30. A chimeric alphavirus comprising mutated capsid protein.

31. A live attenuated chimeric alphavirus comprising mutated capsid protein.

32. A vaccine comprising:

an isolated, purified, synthetic or recombinant alphaviral mutated capsid protein;

an isolated, purified, synthetic or recombinant alphaviral nascent structural polyprotein comprising a mutated capsid protein;

a recombinant alphaviral genome encoding a mutated capsid protein;

a recombinant alphavirus comprising mutated capsid protein;

a live attenuated recombinant alphavirus comprising mutated capsid protein;

a chimeric alphavirus comprising mutated capsid protein; or a live attenuated chimeric alphavirus comprising mutated capsid protein.

33. A sub-unit vaccine comprising: recombinant alphavirus comprising mutated capsid protein; recombinant alphaviral nascent structural polyprotein comprising a mutated capsid protein; or recombinant alphaviral genome encoding a mutated capsid protein.

34. A serum containing alphavirus-neutralising antibodies obtained from a subject immunised with or administered the vaccine of paragraph 32 or paragraph 33, the protein of paragraph 25, the polyprotein of paragraph 26, the genome of paragraph 27, or the alphavirus of any one of paragraphs 28 to 31.

35. At least one alphavirus-neutralising antibody obtained from a subject immunised with the vaccine of paragraph 32 or paragraph 33, the protein of paragraph 25, the polyprotein of paragraph 26, the genome of paragraph 27, or the alphavirus of any one of paragraphs 28 to 31.

36. A pharmaceutical preparation comprising: (1) the protein of paragraph 25 or a pharmaceutically acceptable derivative thereof; (2) the polyprotein of paragraph 26 or a pharmaceutically acceptable derivative thereof; (3) the genome of paragraph 27 or a pharmaceutically acceptable derivative thereof; (4) the alphavirus of any one of paragraphs 28 to 31 or a pharmaceutically acceptable derivative thereof; (5) the vaccine of paragraph 32 or paragraph 33 or a pharmaceutically acceptable derivative thereof; (6) the serum of paragraph 34 or a pharmaceutically acceptable derivative thereof; or (7) the least one alphavirus-neutralising antibody of paragraph 35 or a pharmaceutically acceptable derivative thereof, and at least one pharmaceutically acceptable carrier.

37. An immunogenic composition comprising: (1) the protein of paragraph 25; (2) the polyprotein of paragraph 26; (3) the genome of paragraph 27; (4) the alphavirus of any one of paragraphs 28 to 31; (5) the vaccine of paragraph 32 or paragraph 33; (6) the serum of paragraph 34; or (7) the least one alphavirus-neutralising antibody of paragraph 35.

38. A method of (1) preventing a subject from contracting an alphaviral infection naturally; (2) preventing a subject from developing alphaviral disease; (3) eliciting an alphaviral-protective immune response in a subject; or (4) stimulating an anti-alphaviral immune response in a subject, said method comprising the step of administering to the subject: (1) the protein of paragraph 25; (2) the polyprotein of paragraph 26; (3) the genome of paragraph 27; (4) the alphavirus of any one of paragraphs 28 to 31; or (5) the vaccine of paragraph 32 or paragraph 33.

39. A method of (1) treating a subject having alphaviral disease, or (2) reducing the severity of alphaviral disease, said method comprising the step of administering to the subject: (1) the serum of paragraph 34 or a pharmaceutically acceptable derivative thereof; or (2) the least one alphavirus-neutralising antibody of paragraph 35 or a pharmaceutically acceptable derivative thereof.

40. A method of screening or diagnosing whether a subject has an alphaviral infection or disease, said method comprising the step of: (1) testing the subject, or biological sample obtained from the subject, for reactivity with the serum of paragraph 34 or the at least one alphavirus-neutralising antibody of paragraph 35, wherein reactivity indicates that the subject has an alphaviral infection or disease; and, optionally: (2) treating the subject.

41. An isolated, purified, synthetic or recombinant nucleic acid encoding the alphavirus capsid protein according to paragraph 25 or the polypeptide according to paragraph 26.

42. An isolated, purified, synthetic or recombinant alphaviral genome encoding a mutated capsid protein.

43. A vector comprising the nucleic acid according to paragraph 41 or the genome according to claim 42.

44. A cell comprising the vector according to paragraph 43.

45. A kit for carrying out the method according to any one of paragraphs 38 to 40.

46. A method of preparing (1) the vaccine of paragraph 32 or paragraph 33, or (2) the recombinant alphavirus of any one of paragraphs 28 to 31, said method comprising the steps of: (1) mutating a capsid protein of an alphavirus to produce a recombinant alphavirus; and (2) enabling the recombinant alphavirus to replicate.

47. The protein of paragraph 25, the polyprotein of paragraph 26, the genome of paragraph 27, the alphavirus of any one of paragraphs 28 to 31, the vaccine of paragraph 32 or 33, the serum of paragraph 34, the at least one antibody of paragraph 35, the pharmaceutical preparation of paragraph 36, the immunogenic composition of paragraph 37, the method of any one of paragraphs 38 to 40, the nucleic acid of paragraph 41, the genome of paragraph 42, the vector of paragraph 43, the cell of paragraph 44, the kit of paragraph 45, or the method of paragraph 46, wherein the mutated capsid protein has: a mutated nucleolar localisation region/signal/sequence (NoLS) compared with the wildtype capsid protein; one or more mutations other than in the NoLS; a mutated NoLS as well as one or more mutations other than in the NoLS; one or more amino acids of the NoLS of wild-type CHIKV capsid protein shifted in position, replaced and/or deleted; one or more of amino acid positions 58 to 110 of wild-type CHIKV capsid protein shifted in position, replaced and/or deleted; one or more of amino acid positions 62, 63, 65, 66, 68, 69, 84, 85, 95, 96, 101 and 102 of wild-type CHIKV capsid protein shifted in position, replaced and/or deleted; at least amino acid positions 62, 63, 65, 66, 68, 69, 84, 85, 95, 96, 101 and 102 of wild-type CHIKV capsid protein shifted in position, replaced and/or deleted; or a sequence as shown or as substantially shown in any one of SEQ. ID NOS. 1 and 4 to 7.

48. The invention of any one of paragraphs 25 to 46, wherein the alphaviral mutated capsid protein is derived from an alphavirus such as Ross River virus (RRV), Barmah Forest virus (BFV), O'nyong-nyong virus (ONNV), Mayaro virus (MAYV), Sindbis virus group (causing Pogosta disease, Ockelbo disease and Karelian fever), or Semliki Forest virus (SFV).

49. The method of paragraph 38 or 39, wherein the alphaviral infection or disease is caused by Ross River virus (RRV), Barmah Forest virus (BFV), O'nyong-nyong virus (ONNV), Mayaro virus (MAYV), Sindbis virus group (causing Pogosta disease, Ockelbo disease and Karelian fever) or Semliki Forest virus (SFV), or other type of alphavirus.

BRIEF DESCRIPTION OF FIGURES

FIG. 2 (A) Fluorescence loss in photobleaching (FLIP) analysis performed on live Vero cells transfected with either pCapsid-WTEGFP (labelled "WT") or capsid protein mutants pCapsid-101-EGFP (labelled "101") and pCapsid-NoLSEGFP (labelled "101/95"). (B) Fluorescence loss in the cytoplasm was assessed over a 280 sec period during continual photobleaching of a section of the nucleus. Fluorescence recovery curves were constructed; data were normalized following the bleaching period so that the initial pre-bleaching was set as 1 and the fully bleached fluorescence intensity was set as 0.

FIGS. 4 (A) and (B) Subcellular localisation of capsid protein in CHIKV-WT or CHIKV-NoLS infected mammalian and mosquito cells. Vero (A) or C6/36 (B) cells were infected with CHIKV-WT or CHIKV-NoLS at an MOI 1 pfu/cell. Cells were fixed and permeabilised at 24 h post infection and indirect immunofluorescence performed using capsid protein-specific antibodies. Images are representative of at least 6 fields of view. The white bar represents 15 µm.

FIGS. 4 (C), (D) and (E) CHIKV containing the NoLS mutation in capsid protein shows attenuation in vitro. Multistep growth kinetics in BHK-21 (C) and C6/36 (D) cells were obtained by infecting cells with CHIKV-WT or CHIKV-NoLS at an MOI of 0.1 pfu/cell. Supernatants were collected at indicated time points and infectious virus quantified by plaque assay. , $P<0.01$; *, $P<0.001$ using two-way ANOVA with Bonferroni post-tests. Each symbol represents the mean±standard error for 3 independent experiments. (E) Plaque size (mm) in infected BHK-21 cells. ***, $P<0.001$ using Student's unpaired t-tests. Each symbol represents the diameter of a single plaque.

FIG. 6 (A) Photographs of CHIKV-WT and CHIKV-NoLS infected C57BL/6 mice at day 3 post-infection. (B) Graph showing CHIKV-induced footpad swelling (width x breadth), monitored daily.

FIG. 11. Protein sequence alignment of CHIKV wild-type capsid protein [SEQ. ID NO. 1] and SFV wild-type capsid protein [SEQ. ID NO. 2], with amino acids found important for nucleolar transportation shown in underline.

FIG. 14. CHIKV-NoLS or CHIKV-WT plaque size (mm) plotted against viral passage number in infected Vero cells. Each symbol represents the diameter of a single plaque with the mean±standard deviation.

FIG. 15. Graph of average CHIKV-NoLS titres before and after 0.22 µm filtration. A T-175 flask of P0 CHIKV-NoLS was thawed and the cell suspension was spun at 2000 rpm for 5 min to pellet cell debris. The supernatant (unfiltered) was collected and ~10 ml supernatant was filtered through either a 0.22 µm pore size hydrophilic Polyethersulfone (PES) membrane or 0.22 µm pore size hydrophilic PVDF membrane.

FIG. 16. (A) Graph showing the effect of temperature on the titre of CHIKV-NoLS during long term storage. (B) Graph showing the effect of temperature on the titre of CHIKV-WT during long term storage. CHIKV-NoLS and CHIKV-WT were diluted to $5 \times 10^5$ pfu/ml and vials stored at 21° C., 4° C., −20° C. and −80° C. At the indicated time points infectious CHIKV-NoLS (A) and CHIKV-WT (B) were quantified by plaque assay.

MATERIALS AND METHODS

Site-Directed Mutagenesis of Capsid Protein

Figures 1A, 1B:
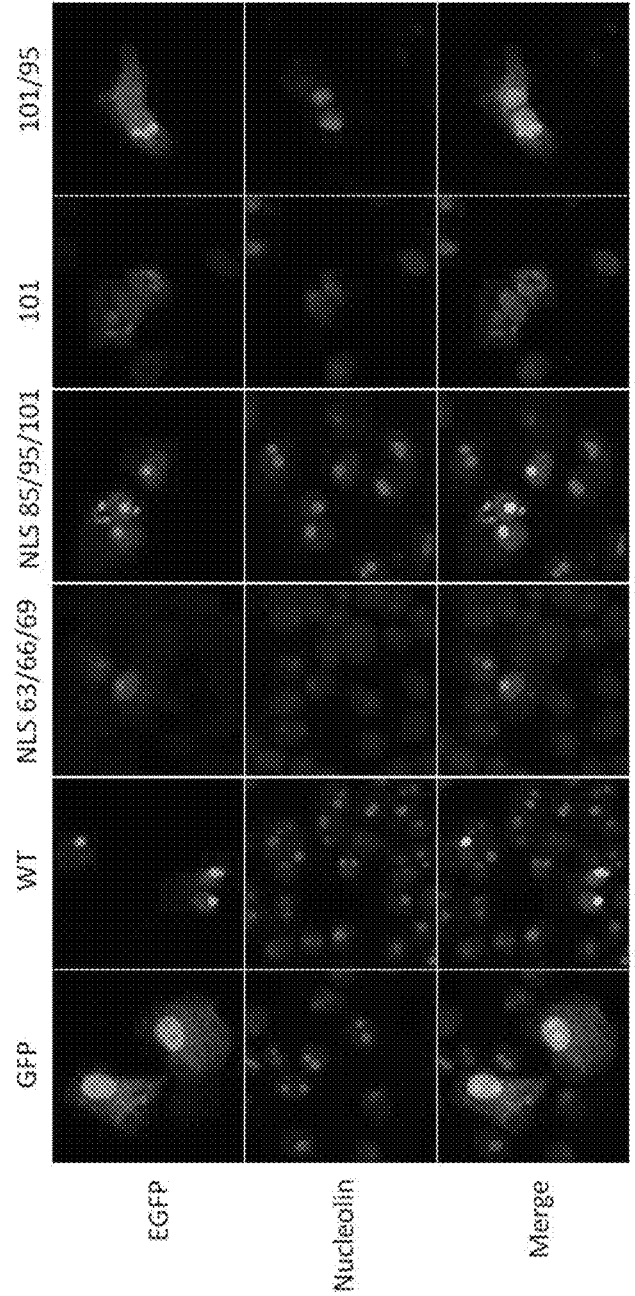
FIG. 1 (A) Partial sequence alignment of wild-type CHIKV capsid protein (WT—also known as "Capsid-WT") [SEQ. ID NO. 3] and mutated CHIKV capsid proteins (Capsid-NLS 63/66/69 [SEQ. ID NO. 4], Capsid-NLS 85/95/101 [SEQ. ID NO. 5], Capsid-101 [SEQ. ID NO. 6] and Capsid-101/95 [SEQ. ID NO. 7]—also known as "Capsid-NoLS"). (B) EGFP-tagged capsid protein subcellular localisation. Vero cells separately transfected with pEGFP, pCapsid-WTEGFP, pCapsid-NLS 63/66/69-EGFP, pCapsid-NLS 85/95/101-EGFP, pCapsid-101-EGFP and pCapsid-NoLSEGFP. Vero cells in the top panel show EGFP (enhanced green fluorescent protein) fluorescence. Vero cells in the middle panel show indirect immunofluorescence using nucleolin-specific antibody. Vero cells in the bottom panel show a merge of the top and middle panels.

Capsid protein cDNA was amplified from the ICRES vector (University of Tartu) and cloned into commercially available EGFP (enhanced GFP) plasmid. Site-directed mutants of CHIKV capsid protein were generated using a QuikChange II site-directed mutagenesis kit (Agilent), as per the manufacturer's instructions.

Western Blot Analysis

Cells were transfected with pEGFP, pCapsid-WTEGFP (wild type capsid protein), or the capsid protein mutants pCapsid-NLS 63/66/69-EGFP, pCapsid-NLS 85/95/101-EGFP, pCapsid-101-EGFP and pCapsid-NoLSEGFP using Lipofectamine® 2000 transfection reagent (Thermo Fisher Scientific) as per the manufacturer's instructions. After 24 h, the cell lysates were analyzed by Western blot analysis using EGFP and Actin-specific antibodies. Actin served as a loading control.

Confocal Imaging

Cells were grown on polylysine-treated coverslips. Cells were fixed in 4% paraformaldehyde and permeabilized in 1% Triton X-100. The cells were then blocked in 1% bovine serum albumin (BSA) made in PBS and incubated at 37° C. for 1 h. Primary antibody, nucleolin, was diluted 1:100 in 1% BSA and incubated with the cells for 1 h at 37° C. Texas Red anti-mouse (Vector Laboratories) was diluted 1:500 in 1% BSA and incubated with the cells for 1 h at 37° C. Coverslips were mounted in Vectorshield mounting medium (Vector Laboratories), and staining was visualized on an Olympus FV1000 confocal microscope.

Live Cell Imaging

Cells were plated on glass-based 33-mm culture dishes and imaged at 24 h post-transfection using an Upright LSM 510 META Axioplan 2 confocal microscope (Zeiss). Cells were maintained at 37° C. and, during imaging, the cell culture medium was exchanged for $CO_2$-independent medium (Thermo Fisher). Fluorescence loss was measured using the ROI mean module of the LSM 510 software.

Flow Cytometry for Cytotoxicity

Transfected cells were collected and stained with 1 µg/mL propidium iodide. Cells were fixed in 4% paraformaldehyde and analysed using the CyAn ADP flow cytometer (Beckman Coutler) with Kaluza software.

Multi Step Growth Kinetics

Cells were infected at a multiplicity of infection (MOI) of 0.1 pfu/cell. Following adsorption of virus for 1 h at 37° C., cell monolayers were washed and fresh growth medium was added. Supernatants were collected at indicated time points and infectious virus quantified by plaque assay.

Ankle Cytokines

RNA was extracted from mouse tissues using TRIzol (Invitrogen, Melbourne, Victoria, Australia) according to the manufacturer's instructions. 1 µg of RNA was reverse transcribed using random primers and reverse transcriptase (Sigma Aldrich, Sydney, Australia) according to the manufacturer's instructions. Quantitative PCR was performed with 50 ng of template cDNA, QuantiTect Primer Assay kits (Qiagen, Hilden, Germany) and SYBR® Green Real-time PCR reagent in a CFX96 Touch™ Real-Time PCR System. Data were normalized to the housekeeping gene HPRT1 and the fold change in messenger RNA (mRNA) expression relative to mock-infected PBS treated samples for each gene was calculated using the $\Delta\Delta Ct$ method. Briefly, $\Delta\Delta Ct = \Delta Ct$ (RRV-infected)$-\Delta Ct$ (Mock-infected) where $\Delta Ct = Ct$ (gene of interest)$-Ct$ (housekeeping gene—HPRT). The fold change for each gene was calculated as $2-\Delta\Delta Ct$.

In Vivo Infections and Disease Monitoring 21-day-old C57BL/6 mice were subcutaneously infected with $10^4$ pfu CHIKV-WT or CHIKV-NoLS in the ventral/lateral side of the foot and monitored daily for signs of CHIKV-induced footpad swelling (width x breadth). Animal experiments were approved by the Animal Ethics Committee of Griffith University (GLY/05/15/AEC). All procedures involving animals conformed to the National Health and Medical Research Council Australian code of practice for the care and use of animals for scientific purposes $8^{th}$ edition 2013.

Viral Titer Assay

Ankle joint and serum were collected and assayed for viral titer using plaque assay. Tissue samples were homogenized in 1 mL of PBS and 10-fold serial dilutions of homogenate and sera were added in triplicate to Vero cells. Virus was allowed to incubate for 1 h at 37° C. in a 5% $CO_2$ incubator before virus was removed and the cells overlaid with OPTI-MEM (Invitrogen, Melbourne, Victoria, Australia) containing 3% FCS and 1% agarose (Sigma Aldrich, Sydney, Australia) and incubated for 48 h in a 5% $CO_2$ incubator. Cells were fixed in 1% formalin and virus plaques were made visible by staining with 0.1% crystal violet.

In Vivo Immunisation and Challenge 21-day-old C57BL/6 mice were subcutaneously immunised with one dose of $10^4$ pfu CHIKV-WT or CHIKV-NoLS in the ventral/lateral side of the foot. At 30 days post immunisation, mice were either challenged with $10^4$ pfu CHIKV-WT in the ventral/lateral side of the foot and monitored daily for signs of CHIKV-induced footpad swelling or $10^4$ pfu Ross River virus (RRV) subcutaneously in the thorax and viraemia measured. Animal experiments were approved by the Animal Ethics Committee of Griffith University (GLY/05/15/AEC). All procedures involving animals conformed to the National Health and Medical Research Council Australian code of practice for the care and use of animals for scientific purposes $8^{th}$ edition 2013.

In Vitro Neutralisation

Pooled mouse sera (n>7) was serially diluted and mixed with CHIKV-ZsGreen (MOI 1) for 2 h before infection of Vero cells for 1 h and incubation at 37° C. for 6 h. Infectivity was measured as % ZsGreen+ve live cells by flow cytometry.

Oligonucleotides, Plasmids, and Antibodies.

To generate pCapsid-EGFP, cDNA corresponding to CHIKV capsid protein was amplified by PCR using primers CHIKCprotF (5' GCGGCGCAAGCTTATGGAGTT-CATCCCAACCC 3'-SEQ. ID NO. 8) and CHIKCprotR (5' CGCGGATCCGACTCTTCGGCCCCCTCG 3'-SEQ. ID NO. 9) and cloned into pEGFP-N1 (Takara Bio USA, Inc.). To generate pCapsidW-EGFP containing tryptophan residue required for capsid protein autoproteolytic cleavage at the C-terminal of capsid protein, primers CHIKCprotF and CHIKCprotWR (5' CGCGGATCCGACCACTCTTCGGCC 3'-SEQ. ID NO. 10) were used and the obtained fragment was cloned into pEGFP-N1. pSP6-CHIKV-ZsGreen, a plasmid containing cDNA of CHIKV variant expressing the ZsGreen marker protein, was constructed using a full-length infectious cDNA clone of the La Reunion CHIKV isolate LR2006-OPY1 as described previously (Pohjala L, Utt A, Varjak M, Lulla A, Merits A, Ahola T, Tammela P. 2011. Inhibitors of Alphavirus Entry and Replication Identified with a Stable Chikungunya Replicon Cell Line and Virus-Based Assays. Plos One 6). Oligonucleotides used in site-directed mutagenesis are listed in Table 1. Mutants were generated using a QuikChange II site-directed mutagenesis kit (Agilent Technologies USA, Inc.). Antibodies to nucleolin (Santa Cruz Biotech USA, Inc.), EGFP (BD Biosciences, USA), and actin (Santa Cruz Biotech USA, Inc.) were purchased from the respective suppliers. Monoclonal capsid protein antibody was made in house and characterised as described previously (Goh L Y H, Hobson-Peters J, Prow N A, Gardner J, Bielefeldt-Ohmann H, Suhrbier A, Hall R A. 2015. Monoclonal antibodies specific for the capsid protein of chikungunya virus suitable for multiple, applications. Journal of General Virology 96:507-512; Goh L Y H, Hobson-Peters J, Prow N A, Baker K, Piyasena T B H, Taylor C T, Rana A, Hastie M L, Gorman J J, Hall R A. 2015. The Chikungunya Virus Capsid Protein Contains Linear B Cell Epitopes in the N- and C-Terminal Regions that are Dependent on an Intact C-Terminus for Antibody Recognition. Viruses-Basel 7:2943-2964. A cocktail of anti-capsid monoclonal antibodies (1.7B2 and 4.1H11) was used for immunofluorescence.

carried out with Lipofectamine 2000 (Thermo Fisher Scientific, Australia) according to the manufacturer's instructions.

Mice

C57BL/6 WT mice were obtained from the Animal Resources Centre (Perth, Australia) and bred in-house. All animal experiments were performed in accordance with the guidelines set out by the Griffith University Animal Ethics Committee. Twenty one-day-old C57BL/6 male and female mice, in equal distribution, were inoculated in the ventral/lateral side of the foot with $10^4$ plaque-forming units (pfu) CHIKV-WT or CHIKV-NoLS diluted in PBS to a volume of 20 µl. Mock-infected mice were inoculated with PBS alone. Mice were weighed and scored for disease signs every 24 h and sacrificed by $CO_2$ asphyxiation at experimental end points. CHIKV-induced footpad swelling was assessed by measuring the height and width of the perimetatarsal area of the hind foot, using Kincrome digital vernier callipers. At 30 days post infection mice were challenged in the ventral/lateral side of the foot with $10^4$ pfu CHIKV-WT, weighed and scored for disease signs every 24 h and viraemia measured at day 1, 2 and 3 post challenge or $10^4$ pfu Ross River virus (RRV) subcutaneously in the thorax and viraemia measured at day 1 and 2 post challenge.

Neutralisation Assay

The neutralising capacity of antibody from CHIKV-WT or CHIKV-NoLS infected mice at day 30 post infection was analysed by immunofluorescence-based cell infection assays using Vero cells and CHIKV-ZsGreen. Infectious virus, taken at an amount sufficient for multiplicity of infection (MOI) 0.4, was mixed with diluted ($10^{-1}$, $10^{-2}$ and $10^{-3}$), heat-inactivated (56° C. for 30 mins) pooled mouse sera,

TABLE 1

Oligonucleotides used in site-directed mutagenesis

| Primer name | Sequence | SEQ. ID NO. |
| --- | --- | --- |
| K84/85A sense | 5' caaaacaacacaaatcaagcggcgcagccacctaaaaagaaac | 11 |
| K84/85A antisense | 3' gttttgttgtgtttagttcgccgcgtcggtggattttttctttg | 12 |
| K95/96A sense | 5' gaaaccggctcaagcggcaaagaagccgggc | 13 |
| K95/96A antisense | 3' cttttggccgagttcgccgtttcttcggcccg | 14 |
| R101/102A sense | 5' gaagccgggcgccgcagagaggatgtgcatgaaaatcg | 15 |
| R101/102A antisense | 3' cttcggcccgcggcgtctctcctacacgtacttttagc | 16 |
| R62/63A sense | 5' gcggtaccccaacagaagccagccgcgaatcggaagaataag | 17 |
| R62/63A antisense | 3' cgccatggggttgtcttcggtcggcgcttagccttcttattc | 18 |
| K68/69A sense | 5' gaatcggaagaatgcggcgcaaaagcaaaaacaacaggcgcc | 19 |
| K68/69A antisense | 3' cttagccttcttacgccgcgttttcgttttttgttgtccgcgg | 20 |
| RK65/66A sense | 5' cagccgcgaatgcggcgaatgcggcgcaaaag | 21 |
| RK65/66A antisense | 3' gtcggcgcttacgccgcttacgccgcgttttc | 22 |

Cell Culture, Transfection and Virus Propagation.

Vero and BHK-21 cells were cultured in Opti-MEM, Gibco® (Thermo Fisher Scientific, Australia), supplemented with 3% fetal calf serum (FCS). C6/36 cells were cultured in Leibovitz's L-15 medium, Gibco® (Thermo Fisher Scientific, Australia), supplemented with 10% tryptose phosphate broth and 10% FCS. Plasmid transfections were followed by incubation for 2 h at 37° C. Virus-antibody mixtures were added to Vero cells and incubated at 37° C. for 1 h. The virus inoculum was removed, cells washed with PBS, and Opti-MEM containing 3% FCS added, followed by incubation for 6 h at 37° C. Cells were gently resuspended, stained with LIVE/DEAD® Near Infrared cell stain (Thermo Fisher Scientific, Australia) and fixed in 4% paraformaldehyde. Infectivity was measured as % ZsGreen+ ve live cells using BD LSR II Fortessa Cell Analyser and quantified with FlowJo software (Treestar USA Inc.).

Immunofluorescence Microscopy and FLIP (Fluorescence Loss in Photobleaching)

Cells grown on polylysine-treated coverslips were fixed in 4% paraformaldehyde and permeabilised in 1% Triton X-100. Cells were then blocked in 1% bovine serum albumin (BSA) made in PBS and incubated at 37° C. for 1 h. Primary antibodies were diluted 1:100 in 1% BSA and incubated with the cells for 1 h at 37° C. Alexa Fluor 647 conjugated secondary antibody, Invitrogen™ (Thermo Fisher Scientific, Australia), was diluted 1:500 in 1% BSA and incubated with the cells for 1 h at 37° C. Coverslips were mounted in Vectorshield mounting medium (Vector Laboratories, USA) and staining was visualised on an Olympus FluoView™ FV1000 confocal microscope. For FLIP analysis, Vero cells were plated on glass-based 33-mm culture dishes and imaged at 24 h post transfection using an LSM 510 META confocal microscope (Zeiss, Oberkochen, Germany). Cells were maintained at 37° C. and, during imaging, the cell culture medium was exchanged for $CO_2$-independent medium, Invitrogen™ (Thermo Fisher Scientific, Australia). Fluorescence loss at the region of interest (ROI) was normalised using the relative fluorescence intensity from the LSM 510 software; initial fluorescence intensity was set as 1.

In Vitro Viral Replication Kinetics

BHK-21 and C6/36 cells were infected with CHIKV-WT or CHIKV-NoLS at MOI 0.1, allowed to incubate for 1 h at 37° C. in a 5% $CO_2$ incubator before virus was removed and the cells washed with PBS and overlaid with Opti-MEM containing 3% FCS. At various times post infection supernatant aliquots were harvested and vial titre measured by plaque assay as outlined below. To determine the virus RNA genome copy number in culture supernatants and virus positive strand RNA copy number in infected cells supernatant was collected and monolayers washed three times in PBS. RNA extraction was performed using TRIzol®, Invitrogen™ (Thermo Fisher Scientific, Australia), according to the manufacturer's instructions. Extracted RNA was reverse transcribed using random nonamer primers and M-MLV reverse transcriptase (Sigma-Aldrich USA, Inc.) according to the manufacturer's instructions. Standard curve was generated using serial dilutions of a full-length infectious cDNA clone of the La Reunion CHIKV isolate LR2006-OPY1. Quantification of viral load was performed using SYBR® Green Real-time PCR reagent in 12.5 μL reaction volume to detect E1 region. Primers CHIKV E1F (5' CCCGGTAAGAGCGGTGAA 3'-SEQ. ID NO. 23) and CHIKV E1R (5' CTTCCGGTATGTCGATG3'-SEQ. ID NO. 24) were used to detect CHIKV genomic, antigenomic and subgenomic RNAs. All reactions were performed using a CFX96 Touch™ Real-Time PCR System. Standard curve was plotted and copy numbers of amplified products were interpolated from standard curve using Graphpad Prism software to determine viral RNA copy number.

Viral Titre Assay

Mice were sacrificed at days 1, 2, 3, and 4 post infection with the ankle joint and serum collected and assayed for viral titre using plaque assay. Tissue samples were homogenised in 1 ml of PBS and 10-fold serial dilutions of homogenate and sera were added in triplicate to Vero cells. Virus was allowed to incubate for 1 h at 37° C. in a 5% $CO_2$ incubator before virus was removed and the cells overlaid with Opti-MEM containing 3% FCS and 1 agarose (Sigma-Aldrich USA, Inc.) and incubated for 48 h in a 5% $CO_2$ incubator. Cells were fixed in 1% formalin and virus plaques were made visible by staining with 0.1% crystal violet. Results were expressed as pfu/ml or pfu per gram of tissue (pfu/g).

Quantitative RT-PCR

RNA was extracted from tissues using TRIzol®, Invitrogen™ (Thermo Fisher Scientific, Australia), according to the manufacturer's instructions. 1 μg of total RNA was reverse transcribed using random nonamer primers and M-MLV reverse transcriptase (Sigma-Aldrich USA, Inc.) according to the manufacturer's instructions. Quantitative PCR was performed with 50 ng of template cDNA, QuantiTect Primer Assay kits (Qiagen, Hilden, Germany) and SYBR® Green Real-time PCR reagent in a CFX96 Touch™ Real-Time PCR System using a standard three-step melt program (95° C. for 15 s, 55° C. for 30 s and 72° C. for 30 s). Data were normalised to HPRT1 and the fold change in mRNA expression relative to mock-infected PBS treated samples for each gene was calculated using the $\Delta\Delta C_T$ method. Briefly, $\Delta\Delta C_T = \Delta C_T$ (Virus infected)$-\Delta C_T$ (Mock infected) where $\Delta C_T = C_T$ (gene of interest)$-CT$ (housekeeping gene). The fold change for each gene is calculated as $2^{-\Delta\Delta C_T}$.

Statistical Analysis

Two-way ANOVA with Bonferroni post-tests was used to examine in vitro viral growth kinetic data and viraemia. Student's unpaired t-tests were used to analyse quantitative RT-PCR and ankle titers at day 3 post infection. One-way ANOVA with Bonferroni post-tests was used to examine neutralisation assay. A P-value <0.05 was considered to be significant.

Results and Discussion

Example 1—Identification of the CHIKV Capsid Protein Nucleolar Localisation Sequence In order to identify the minimal CHIKV capsid protein nucleolar localisation sequence (NoLS), site-directed mutagenesis was performed on recombinant EGFP-tagged CHIKV capsid protein at a region in the N-terminus rich in basic amino acids. Amino acids of the protein were replaced with alanine. Ten amino acids, constituting the minimal NoLS of the CHIKV capsid protein, were identified.

Four mutant capsid proteins were generated and their sequence differences are shown in the sequence alignment of FIG. 1(A) together with the sequence of wild-type CHIKV Capsid protein ("Capsid-WT", labelled as "WT"). The mutated CHIKV capsid proteins were Capsid-NLS 63/66/69 (labelled "NLS 63/66/69"), Capsid-NLS 85/95/101 (labelled "NLS 85/95/10"), Capsid-101 (labelled "101"), and Capsid-101/95 (labelled "101/95") which will also be referred to herein as "Capsid-NoLS".

The 10 amino acid changes in Capsid-101/95 are likely to be the minimal residues required for nucleolar localisation of the capsid protein.

Example 2—Subcellular Localisation of Mutant CHIKV Capsid Proteins

The subcellular localisation of the mutant capsid proteins in Vero cells was investigated using confocal microscopy. As seen in FIG. 1(B), Capsid-WT (labelled as "WT") localised to the nucleolus. Capsid-101 (labelled as "101") showed a reduced ability to localise to the nucleolus, but was still observed in the nucleolus. Capsid-101/95 (labelled as "101/95") comprised the minimal nucleolar localisation sequence and showed a complete absence from the nucleolus.

Figures 4A, 4B:
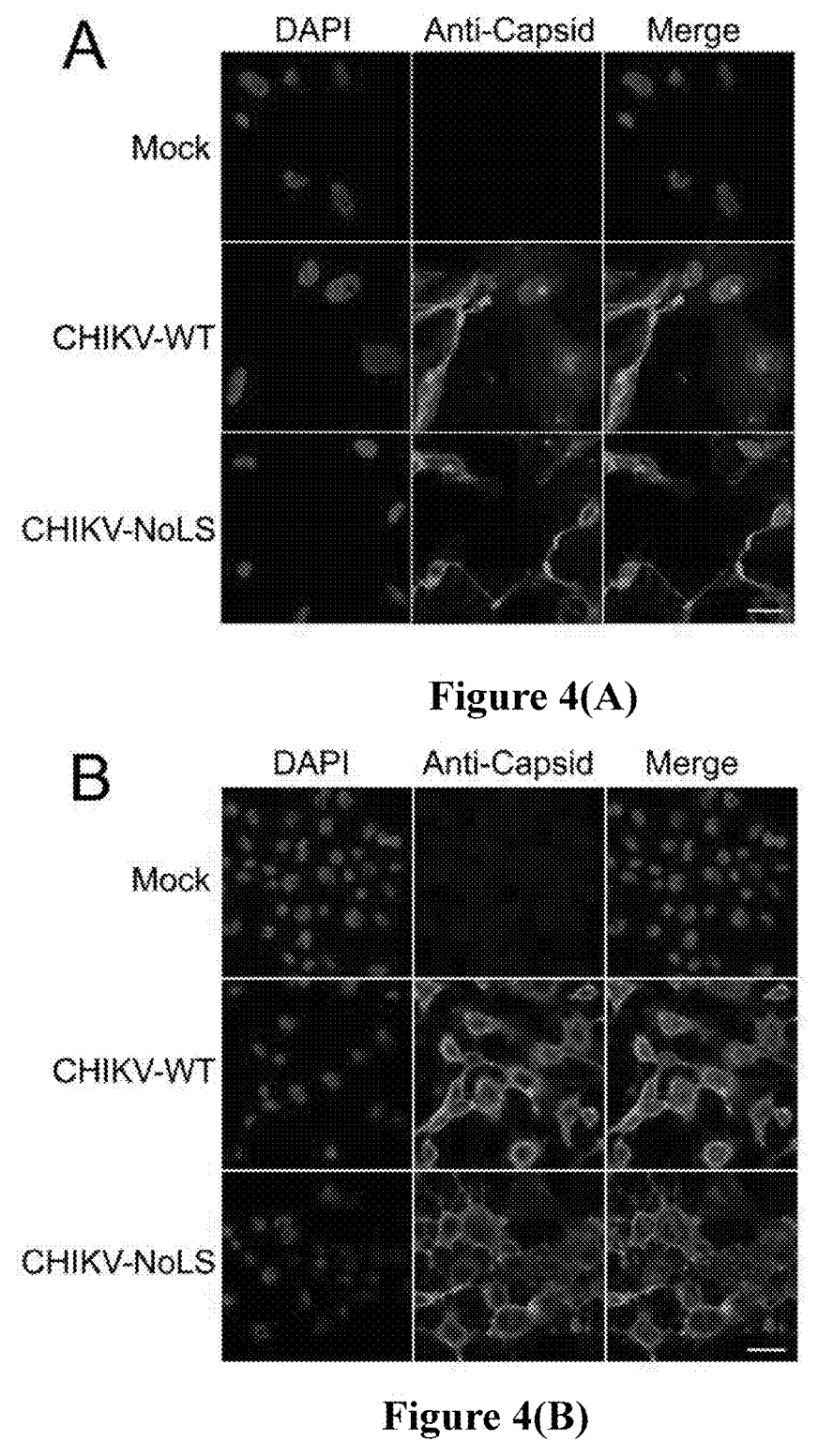

Indirect immunofluorescence, using capsid-specific antibodies, was further used to analyse the subcellular localisation of CHIKV capsid protein in CHIKV-WT and CHIKV-NoLS infected Vero cells and mosquito (*Aedes albopictus*) derived C6/36 cells. Results show that in CHIKV-WT infected Vero cells capsid protein accumulates in subnuclear bodies reminiscent of the nucleolus at 24 h post infection (FIG. 4A). In CHIKV-NoLS infected Vero cells these punctae are absent. Thus, in the context of the virus the NoLS mutation causes similar disruption of capsid protein subnuclear localisation in infected Vero cells. The NoLS mutation is therefore stable in the virus, resulting in a phenotypic disruption of capsid protein subnuclear localisation.

Figure 12:
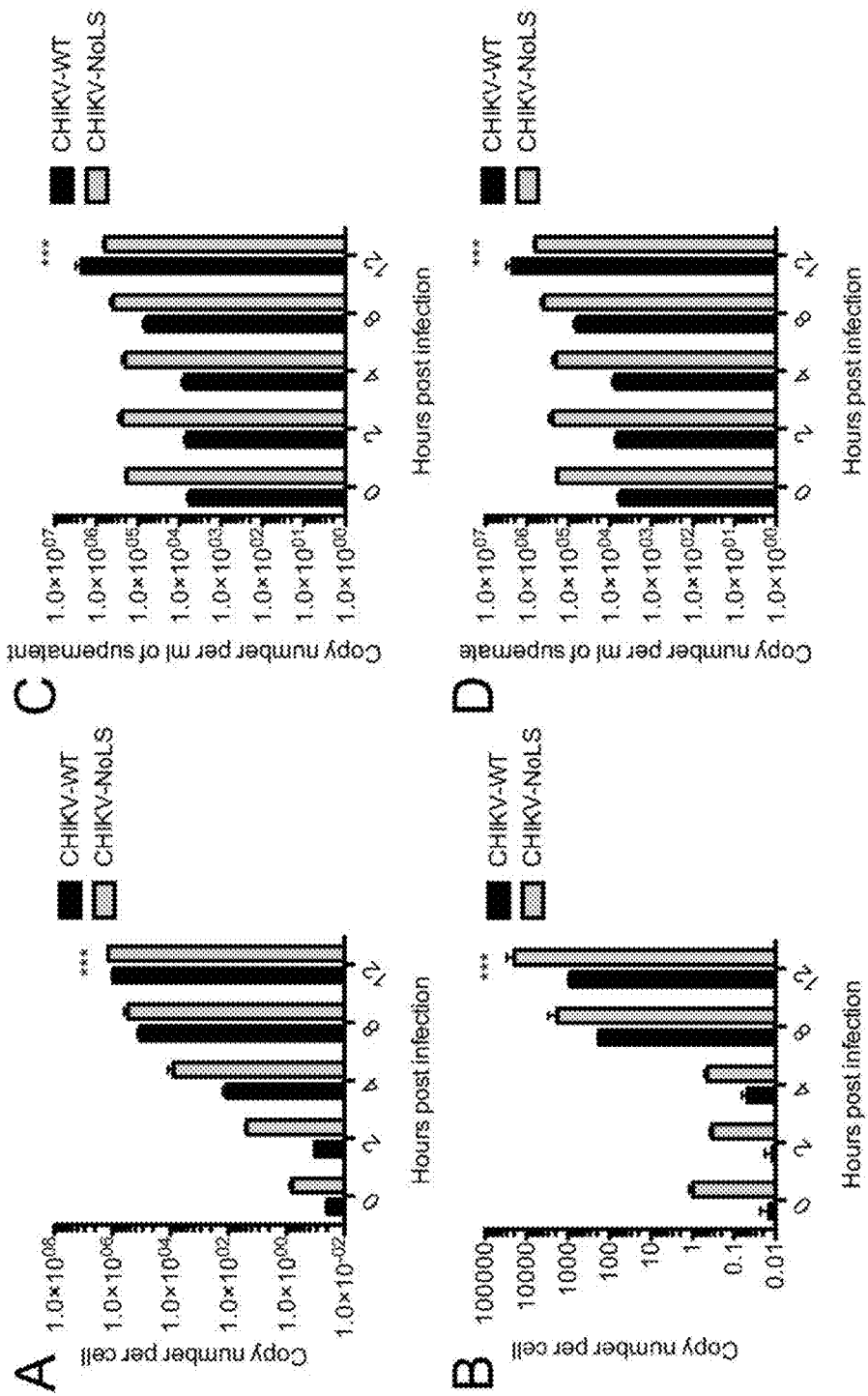
FIG. 12. CHIKV RNA synthesis is not affected by mutation of the capsid protein NoLS. BHK-21 and C6/36 cells were infected with CHIKV-WT or CHIKV-NoLS at an MOI of 0.1 pfu/cell. The viral genome copy number in the culture supernatants and viral RNA copy number in infected cells were determined by quantitative RT-PCR at the indicated times post infection. (A) BHK-21 cell-associated virus, (B) C6/36 cell-associated virus, (C) BHK-21 culture supernatant, (D) C6/36 culture supernatant. ***, $P<0.001$ using two-way ANOVA with Bonferroni post-tests. Each bar represents the mean±standard error for 3 independent experiments.

Interestingly, in CHIKV-WT infected C6/36 cells capsid protein did not accumulate in subnuclear bodies and was found predominantly in the cytoplasm at 24 h post infection (FIG. 12B). In CHIKV-NoLS infected C6/36 cells capsid protein was also found to predominate in the cytoplasm, similar to the localisation observed in CHIKV-WT infected C6/36 cells. Subnuclear localisation of capsid protein is therefore not a characteristic of CHIKV infection in insect cells and mutation of the NoLS has no effect on the subcellular localisation of capsid protein in infected C6/36 cells.

Example 3—Trafficking Ability of Mutant CHIKV Capsid Protein

Fluorescence loss in photobleaching (FLIP) analysis was performed on live Vero cells transfected with either EGFP-tagged wild-type capsid protein or the capsid protein mutants. FLIP analysis was used to investigate the mobility of Capsid-101/95 (labelled "101/95") compared to Capsid-WT (labelled "wt") and mutant Capsid-101 (labelled "101"). Fluorescence loss in the cytoplasm was assessed over a 280 sec period during continual photobleaching of a section of the nucleus. This allowed analysis of the nuclear trafficking rates of the mutants. Fluorescence recovery curves were constructed; data were normalized following the bleaching period so that the initial prebleaching was set as 1 and the fully bleached fluorescence intensity was set as 0.

As seen in FIGS. 2(A) and (B), Capsid-WT showed almost total fluorescence loss after 280 sec, indicating mobility of the protein and trafficking into the nucleus from the cytoplasm. However, mutants Capsid-101 and Capsid-101/95 showed a distinct inability to traffic to the nucleus with fluorescence intensity remaining relatively high. At later times there also appeared to be a cumulative effect of the additional mutations, with Capsid-101/95 more immobile than Capsid-101. These results suggest that mutation of the nucleolar localisation sequence has a major effect on the trafficking ability of capsid protein and perhaps consequently on its subcellular localization.

Figure 3:
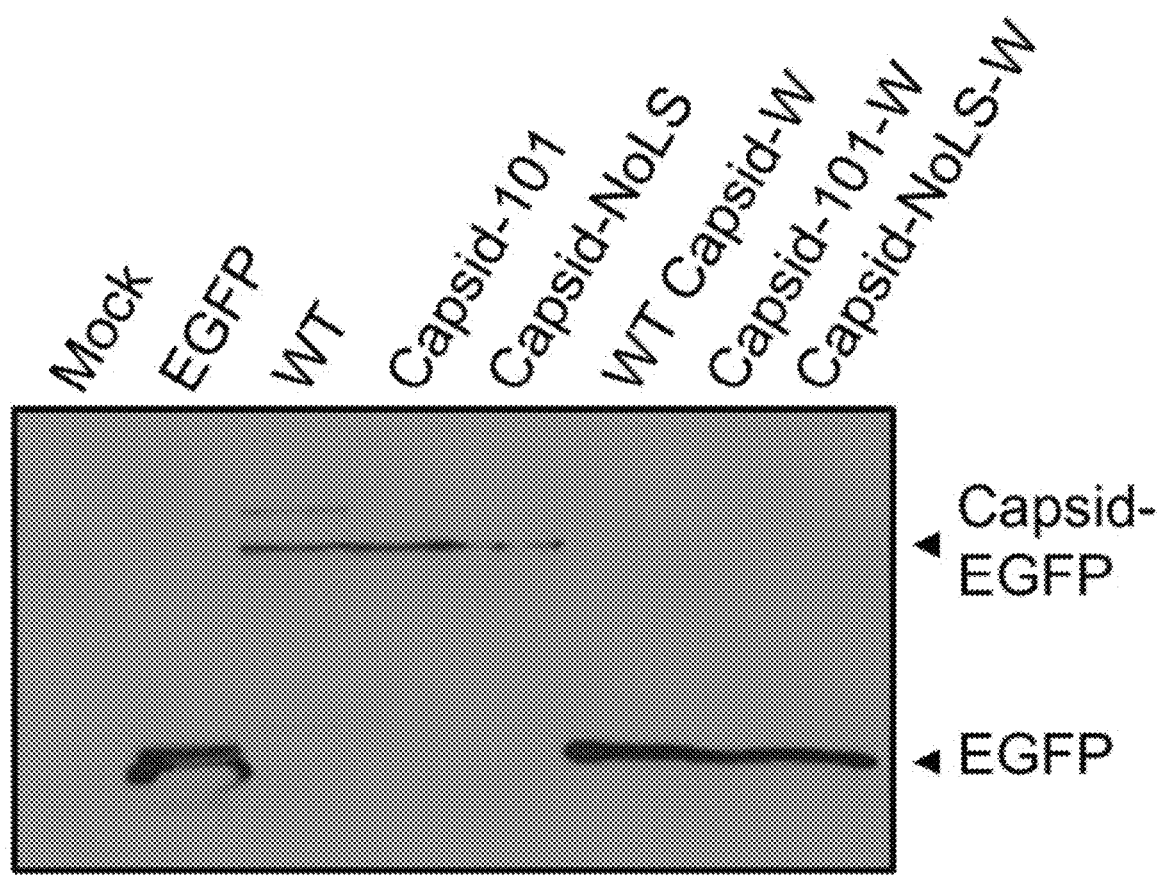
FIG. 3 Mutation of capsid protein NoLS does not affect capsid protein autoprotease activity. Vero cells were transfected with pEGFP, pCapsid-EGFP, pCapsid-101-EGFP or pCapsid-NoLS-EGFP or plasmids expressing EGFP-tagged WT Capsid-W, Capsid-101-W and Capsid-NoLS-W. EGFP-tagged WT Capsid-W, Capsid-101-W and Capsid-NoLS-W contain the C-terminal tryptophan (W261) required for capsid protein autoproteolytic cleavage. Cells were lysed at 24 h post transfection and cell lysates were analysed for cleavage of EGFP from capsid protein by Western blot and EGFP-specific antibody.
Figure 5C:
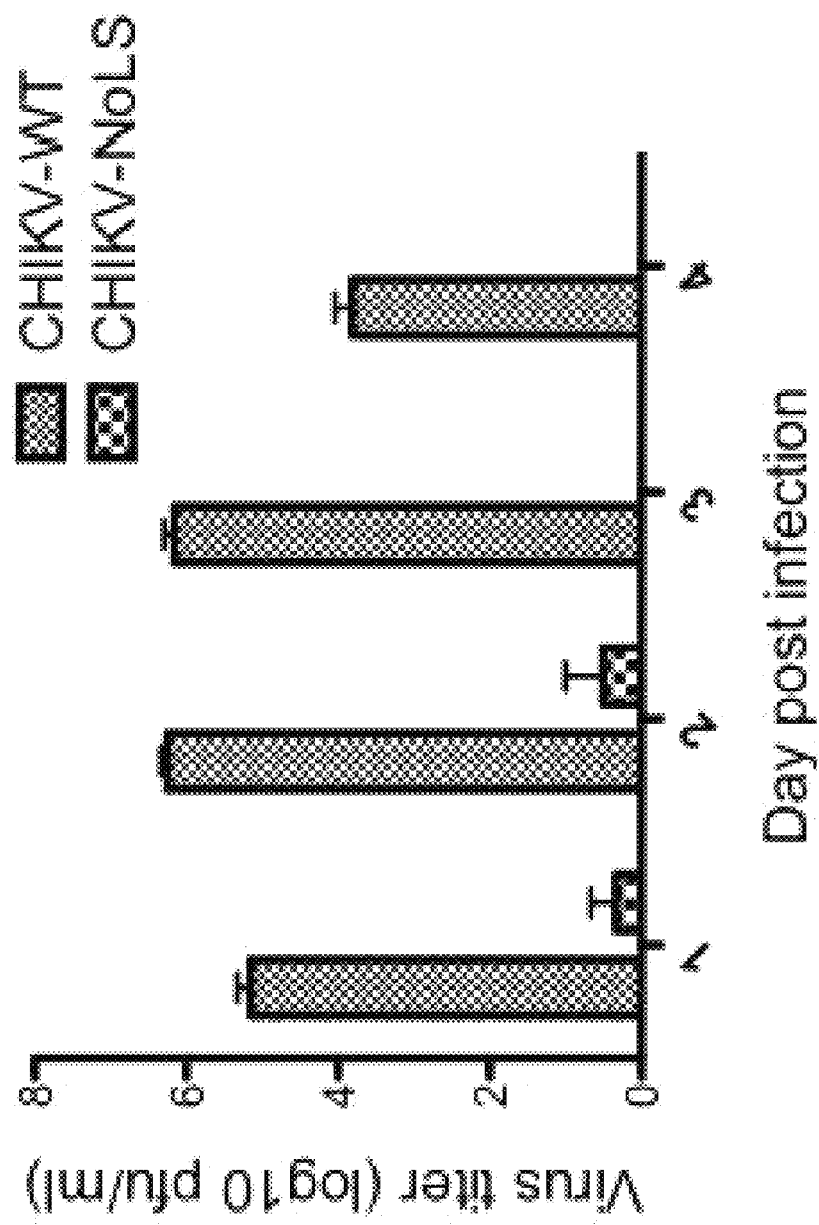
FIG. 5. Viraemia post infection. (A) Graphs showing CHIKV-WT and CHIKV-NoLS viral titers in ankle joint of CHIKV-infected mice at day 3 post-infection, titrated by plaque assay. (B) Graphs showing mRNA expression of inflammatory mediators of CHIKV disease in the ankle joint as analysed by qRT-PCR at day 3 post-infection, the inflammatory mediators being monocyte chemoattractant protein-1 (MCP-1), interferon gamma (IFNγ) and tumor necrosis factor alpha (TNFα). (C) Graph showing CHIKV-WT and CHIKV-NoLS viral titers in serum and ankle joint of CHIKV-infected mice post-infection, titrated by plaque assay.

Example 4—Mutation of the NoLS Did not Affect Capsid Protein Autoproteolytic Cleavage Mutation of the NoLS and its effect on capsid protein autoprotease activity was analysed. Constructs expressing EGFP-tagged WT Capsid-W, Capsid-101-W and Capsid-NoLS-W, containing the C-terminal tryptophan (W261) required for capsid protein autoproteolytic cleavage, were generated. FIG. 3 shows that all constructs lacking W261 residue from the conserved cleavage site were unable to cleave EGFP from capsid protein. However, capsid protease efficiently cleaved EGFP from capsid protein in all constructs that contained W261, including the NoLS mutants of capsid protein (FIG. 3). Thus, mutation of the NoLS has no effect on the autocatalytic protease activity of CHIKV capsid protein.

Example 5—CHIKV Containing the NOLs Mutation in Capsid Protein Shows Attenuation In Vitro To assess the importance of capsid protein nucleolar localisation on CHIKV replication, the effect of the NoLS mutation in the context of a full-length CHIKV infectious clone-derived virus was examined. CHIKV containing the NoLS mutation in capsid protein (CHIKV-NoLS) was rescued and propagated in Vero cells. Plaque purification of virus and Sanger sequencing of the entire CHIKV genome confirmed the NoLS mutation was maintained in passaged virus in the absence of additional mutations. Indirect immunofluorescence, using capsid-specific antibodies, was used to analyse the subcellular localisation of CHIKV capsid protein in CHIKV-WT and CHIKV-NoLS infected Vero cells and mosquito (*Aedes albopictus*) derived C6/36 cells.

Results show that in CHIKV-WT infected Vero cells capsid protein accumulates in subnuclear bodies reminiscent of the nucleolus at 24 h post infection (FIG. 4A). In CHIKV-NoLS infected Vero cells these punctae are absent. Thus, in the context of the virus the NoLS mutation causes similar disruption of capsid protein subnuclear localisation in infected Vero cells. The NoLS mutation is therefore stable in the virus, resulting in a phenotypic disruption of capsid protein subnuclear localisation. Interestingly, in CHIKV-WT infected C6/36 cells capsid protein did not accumulate in subnuclear bodies and was found predominantly in the cytoplasm at 24 h post infection (FIG. 4B). In CHIKV-NoLS infected C6/36 cells capsid protein was also found to predominate in the cytoplasm, similar to the localisation observed in CHIKV-WT infected C6/36 cells. Subnuclear localisation of capsid protein is therefore not a characteristic of CHIKV infection in insect cells and mutation of the NoLS has no effect on the subcellular localisation of capsid protein in infected C6/36 cells.

To examine the replication kinetics of CHIKV-WT and CHIKV-NoLS in mammalian (BHK-21) and mosquito (C6/36) cells, cells were infected at a multiplicity of infection (MOI) of 0.1 pfu/cell and multistep growth kinetics analysed. CHIKV-NoLS grew to significantly lower titers than CHIKV-WT in both BHK-21 cells (FIG. 4C) and C6/36 cells (FIG. 4D). Furthermore, CHIKV-NoLS had a small plaque phenotype in BHK-21 cells (FIG. 4E), indicating a reduced ability of the virus to spread from the initial site of infection and thus attenuation.

Example 6—CHIKV Mutant Capsid Protein—Effect on Disease and Viraemia

Viral titers in serum and ankle joint, and expression of inflammatory mediators of CHIKV disease, were investigated in mutant Capsid-101/95 infected mice. The results are shown in FIGS. 5(A) to (C) and FIGS. 6(A) and (B). Viral titers in serum and ankle joint, and expression of inflammatory mediators of CHIKV disease in Capsid-101/95 infected mice were significantly reduced compared to Capsid-WT infected mice.

At day 3 post-infection the expression of inflammatory mediators of CHIKV disease in the ankle joint was analysed by qRT-PCR. Monocyte chemoattractant protein-1 (MCP-1), interferon gamma (IFNγ) and tumor necrosis factor alpha (TNFα) were dramatically under expressed in the ankle tissue of Capsid-101/95 (labelled "CHIKV-NoLS") infected mice compared to Capsid-WT (labelled "CHIKV-WT") infected mice (see FIG. 5(B)). These soluble immune mediators are key markers of disease progression and severity in CHIKV infected mice. Low expression of these mediators is likely linked to the lack of disease signs in Capsid-101/95 (CHIKV-NoLS) infected mice.

The amount of infectious virus in the blood and joint tissue is intimately linked to disease severity in CHIKV-infected mice. At day 3 post-infection the amount of live virus in the serum and ankle tissue of Capsid-101/95 (CHIKV-NoLS) infected mice was dramatically reduced compared to Capsid-WT (labelled "CHIKV-WT") infected mice (see FIG. 5(A)). Reduced Capsid-101/95 (CHIKV-NoLS) titers are also likely linked to the reduced disease severity in Capsid-101/95 (CHIKV-NoLS) infected mice.

As seen in FIGS. 6(A) and (B), Capsid-101/95 (CHIKV-NoLS) infected mice showed no signs of acute CHIKV disease. Capsid-101/95 (CHIKV-NoLS) infected mice developed no footpad swelling. The results suggest that Capsid-101/95 (CHIKV-NoLS) is highly attenuated in mice. With low reactogenicity, Capsid-101/95 (CHIKV-NoLS) is a suitable candidate for a live attenuated vaccine.

Example 7—Mice Immunised with CHIKV Capsid Protein Show Protective Immunity

Figure 7C:
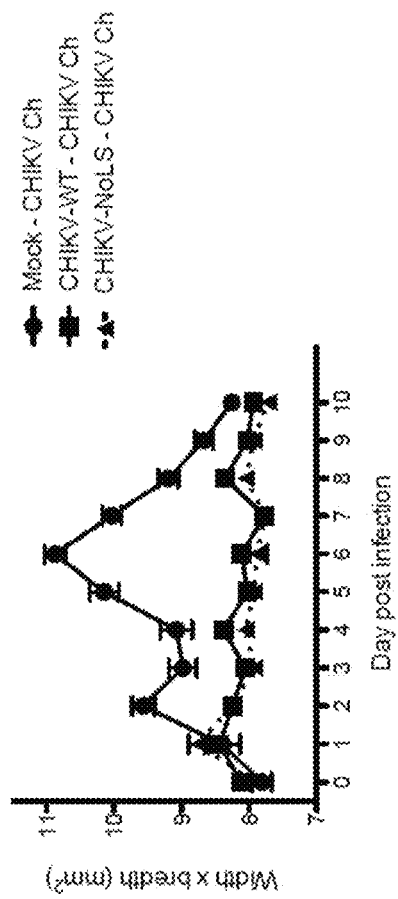
FIG. 7 (A) Photographs of challenged/infected CHIKV-NoLS immunised C57BL/6 mice at day 6 post-challenge/infection. The photograph on the left shows a mock challenge, the middle photograph shows CHIKV-NoLS immunised mice challenged with CHIKV-WT (labelled "WT Challenge"), and the photograph on the right shows CHIKV-NoLS immunised mice challenged with CHIKV-NoLS (labelled "NoLS Challenge"). (B) Graph showing CHIKV titer of CHIKV-NoLS immunised mice challenged with CHIKV-WT (labelled "WT Challenge"), CHIKV-NoLS (labelled "NoLS Challenge") or mock challenge. (C) Graph showing CHIKV-induced footpad swelling (width x breadth) of challenged/infected CHIKV-NoLS immunised mice, monitored daily—mock challenge (labelled "Mock-CHIKV Ch"), CHIKV-WT challenge (labelled "CHIKV-WT-CHIKV Ch"), and CHIKV-NoLS challenge (labelled "CHIKV-NoLS-CHIKV Ch").
Figure 7A:
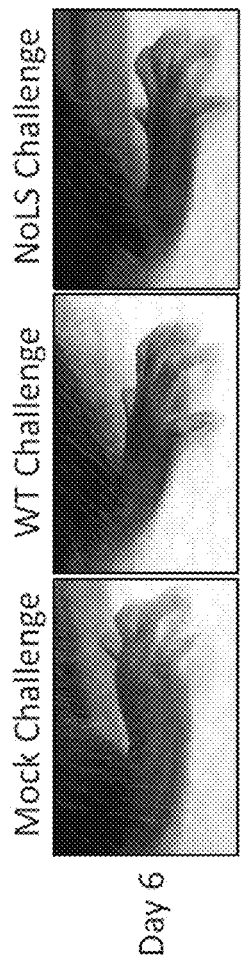
Figure 7B:
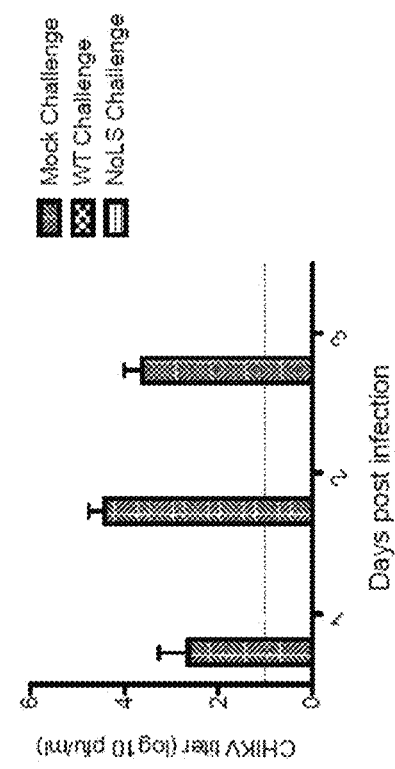

As seen in FIGS. 7(A) to (C), Capsid-101/95 (CHIKV-NoLS) immunised mice were protected from CHIKV disease when challenged with Capsid-WT (labelled "CHIKV-WT"). Mice immunised with Capsid-101/95 (CHIKV-NoLS) showed no signs of footpad swelling upon challenge with Capsid-WT at day 30 post immunisation (see FIG. 7(C)) and developed no detectable viraemia from days 1-3 post challenge (see FIG. 7(B)). Immunisation with CHIKV-NoLS protected mice from CHIKV challenge for up to 30 days, indicating Capsid-101/95 (CHIKV-NoLS) is immunogenic after one dose and immunity is long lived.

Figures 8A, 8B:
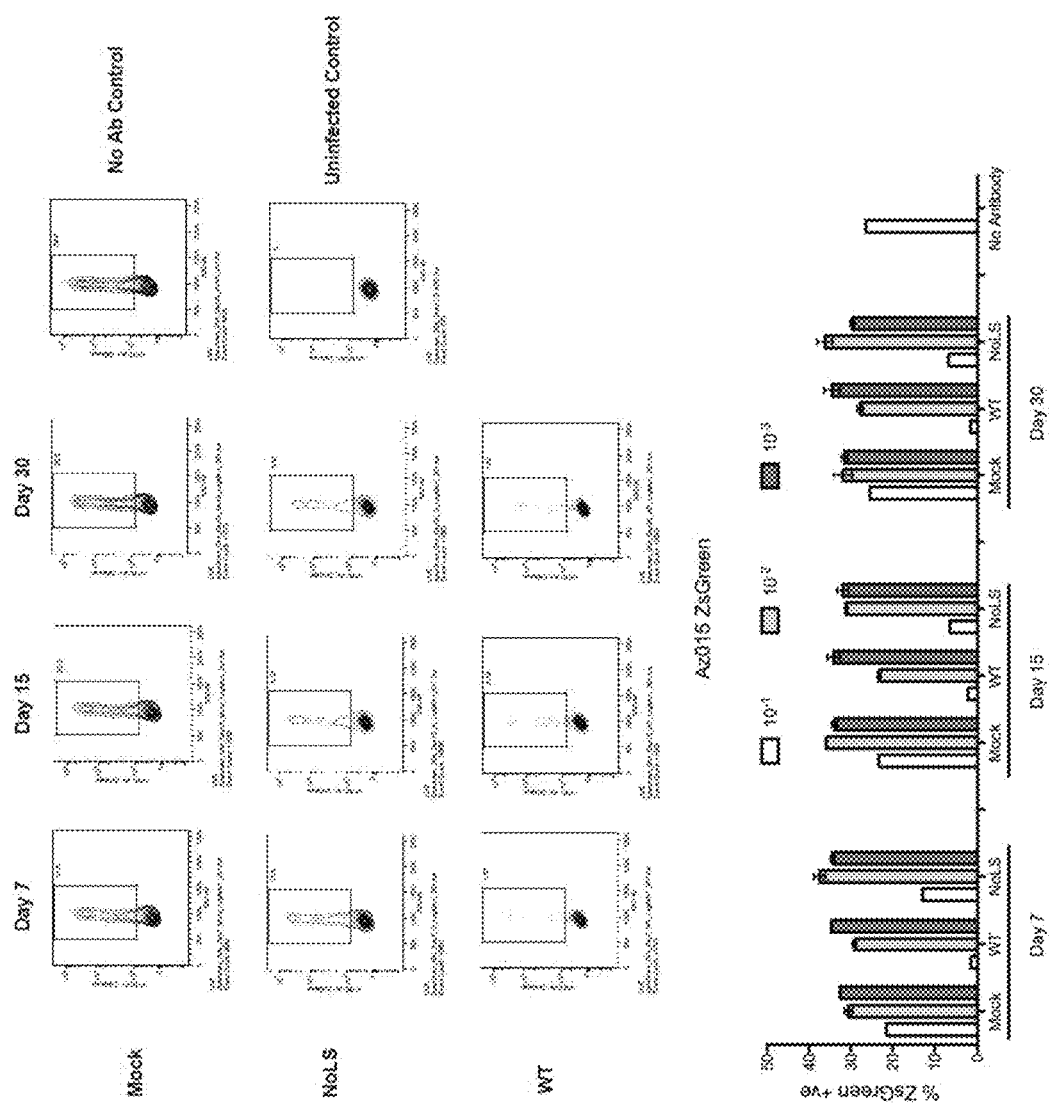
FIG. 8. Neutralising capacity of pooled mouse sera collected at day 7, 15 and 30 post-infection with mock challenge (labelled "Mock"), CHIKV-WT challenge (labelled "WT"), and CHIKV-NoLS challenge (labelled "NoLS"). (A) Pooled mouse sera (n>7) was serially diluted and mixed with CHIKV-ZsGreen (MOI 1) for 2 hours before infection of Vero cells for 1 hour and incubation at 37° C. for six hours. Infectivity was measured as % ZsGreen+ve live cells by flow cytometry. (B) Graph showing % ZsGreen+ve live cells at days 7, 15 and 30.

Example 8—Sera from CHIKV Capsid Protein Infected Mice Neutralise Infectious CHIKV As seen in FIGS. 8(A) and (B), sera from Capsid-101/95 (CHIKV-NoLS) infected mice preincubated with CHIKV was able to neutralise infectious CHIKV in vitro. Antibodies induced by Capsid-101/95 (CHIKV-NoLS) infection efficiently neutralised CHIKV in vitro.

Figure 9:
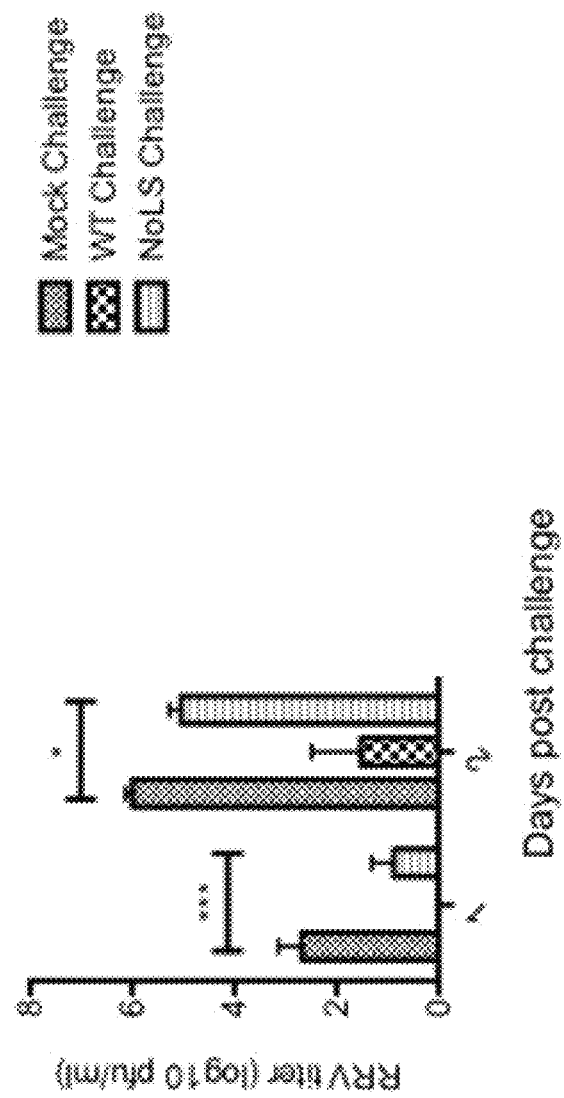
FIG. 9. Graph showing the ability of CHIKV-NoLS immunised mice (day 30 post immunisation) to protect against the development of viraemia following Ross River virus (RRV) challenge—mock challenge (labelled "Mock Challenge"), CHIKV-WT challenge (labelled "WT Challenge"), and CHIKV-NoLS challenge (labelled "NoLS Challenge"). 2way ANOVA with Bonferoni post test; ***$P<0.001$; *$P<0.05$.
Figure 10:
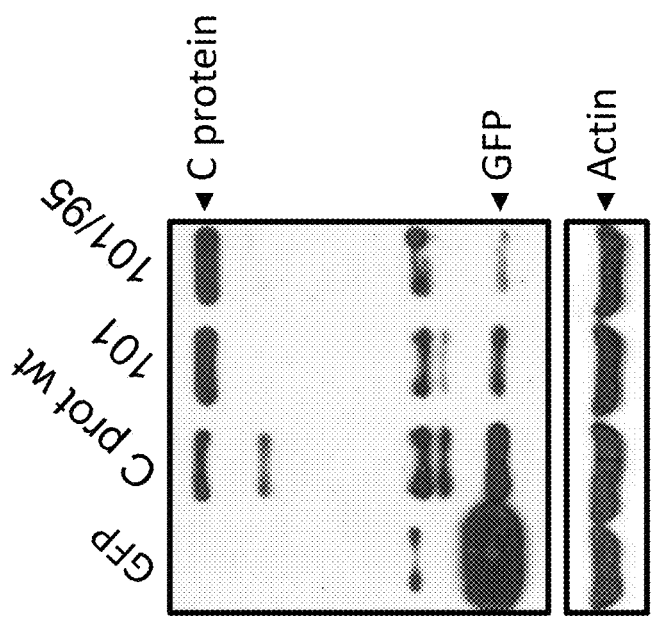
FIG. 10. Western blot of capsid protein EGFP-tagged constructs to confirm expression levels in Vero cells. The blot compares the expression levels of pEGFP (labelled "GFP"), pCapsid-WTEGFP (labelled "C prot wt"), pCapsid-101-EGFP (labelled "101") and pCapsid-NoLSEGFP (labelled "101/95") using EGFP and Actin-specific antibodies. Actin was used as a load control.

Example 9—CHIKV Capsid Protein Immunisation Reduces Peak Viraemia in Ross River Virus Challenged Mice As seen in FIG. 9, Capsid-101/95 (CHIKV-NoLS) immunisation reduced peak viraemia in Ross River virus (RRV) challenged mice. Capsid-101/95 (CHIKV-NoLS) immunised mice showed significantly reduced peak (day 2) and early viraemia, day 1 and 2 post challenge, upon challenge with related alphavirus RRV. By reducing viraemia, an indicator of disease outcome, Capsid-101/95 (CHIKV-NoLS) has the potential to offer cross protection against the disease caused by other arthritogenic alphaviruses such as RRV, BFV, SFV, MAYV and/or ONNV.

Example 10—CHIKV Capsid Protein Immunisation Reduces Peak Viraemia in Ross River Virus Challenged Mice To determine whether the mutant CHIKV capsid proteins Capsid-101 (labelled "101") and Capsid-101/95 (labelled "101/95") expressed at levels similar to the wild-type Capsid-WT (labelled "C prot wt"), each mutant was transfected into Vero cells, and cell lysates were assayed by Western blot analysis using an GFP-specific antibody and, loading control, Actin antibody. The results showed that both Capsid-101 (labelled "101") and Capsid-101/95 (labelled "101/95") expressed at levels similar to that for the wild-type capsid protein Capsid-WT.

Example 11—SFV Capsid Protein NoLS

The SFV capsid protein is the only other alphavirus capsid protein currently known to localise to the nucleolus. [Favre D1, Studer E, Michel M R. Arch Virol. 1994; 137(1-2):149-55. Two nucleolar targeting signals present in the N-terminal part of Semliki Forest virus capsid protein]. Two nucleolar targeting signals have previously been identified in the N-terminal part of the SFV capsid protein.

FIG. 11 shows a protein sequence alignment of CHIKV wild-type capsid protein and SFV wild-type capsid protein, with CHKV amino acids found important for nucleolar transportation shown in underline. Based on the CHIKV and SFV sequence similarities, a mutated SFV capsid protein could be developed which would not localise within the nucleolus—that is, SFV mutant capsid proteins similar to the mutant CHIKV capsid proteins Capsid-101 and Capsid-101/95 could be developed. Mutation of the NoLS of SFV the capsid protein would attenuate its replication and subsequently act as a SFV vaccine and offer cross protection to other alphaviruses.

Example 12—Cross-Reactivity of Alphavirus Antibodies and Chimeric Alphavirus

A growing body of evidence indicates cross-reactivity of alphavirus antibodies with broadly neutralising effects both in vitro and in vivo. A live attenuated vaccine comprising mutated CHIKV capsid protein is likely to offer cross protection against other arthritogenic alphaviruses, such as RRV, BFV, SFV, ONNV and MAYV, which share a greater degree of structural and genetic homology to CHIKV than other types of alphaviruses. It is less likely to be effective against encephalitic alphaviruses, such as Eastern equine encephalitis virus (EEEV) and Venezuelan equine encephalitis virus (VEEV), which are more distantly related. For this reason, a chimeric alphavirus may be constructed (such as taught by Roy C J, Adams A P, Wang E, Leal G, Seymour R L, Sivasubramani S K, Mega W, Frolov I, Didier P J, Weaver S C. Vaccine. 2013. A chimeric Sindbis-based vaccine protects cynomolgus macaques against a lethal aerosol challenge of eastern equine encephalitis virus.), containing all or part of the structural polyprotein or non-structural polyprotein of an encephalitic alphavirus and, for example, the NoLS mutant capsid protein of CHIKV. On this point, it must be remembered that the entire structural polyprotein of alphaviruses can be swapped from one alphavirus to another forming chimeric viruses. A chimeric alphavirus containing the CHIKV capsid with the NoLS mutation may offer much better vaccine protection, greater immunogenicity and/or neutralisation to the desired alphavirus, for not only arthritogenic alphaviruses but also encephalitic alphaviruses (subject to a similar level of attenuation).

Example 13—Identification of Antibody Subtypes

The humoral and cellular responses in subjects following vaccination with a mutant CHIKV capsid protein (or other alphaviral capsid protein) can be measured. A global view of antibody responses (i.e. identify different antibody subtypes) can be obtained. It is likely that the live attenuated recombinant vaccine will induce a strong antibody response with some antibody subtypes dominating the response. Identifying these antibody subtypes associated with strong neutralization may have diagnostic value. For instance, the absence of CHIKV-specific antibody subtype in an unvaccinated subject infected with CHIKV may serve as a specific marker of subjects with increased risk of developing severe disease that can progress to chronic disease. Also, any antibody subtype identified as neutralizing can be administered to subjects with high viremia. The vaccine may also influence cellular response and T cell responses which can also be measured.

Example 14—Attenuation of CHIKV NoLs in Mammalian and Insect Cells Based on Synthesis of Viral RNA and Virus Gene Copy Number To further investigate the attenuation of CHIKV-NoLS in mammalian and insect cells, complementary RT-qPCR analysis of virus genome copy number in the culture supernatants and virus RNA copy number in infected cells was performed. Results suggest that synthesis of viral RNA remains unperturbed by the NoLS mutation in both BHK-21 (FIG. 12A) and C6/36 (FIG. 12B) cells. Furthermore, by 12 h post infection the copy number of CHIKV-NoLS RNAs in infected BHK-21 (FIG. 12A) and C6/36 (FIG. 12B) cells significantly exceeded these in CHIKV-WT infected cells. The difference is potentially due to increased survival of CHIKV-NoLS infected cells allowing prolonged or more efficient synthesis of viral RNA and/or due to reduced competition between viral replicase and capsid protein for binding viral genomic RNAs. However, the genome copy numbers of CHIKV-NoLS in culture supernatants did not show any increase up to 12 h post infection in both BHK-21 (FIG. 12C) and C6/36 (FIG. 12D) cells indicating that no or very little virus was released. This result correlates with the delayed release and reduced titers of infectious CHIKV-NoLS recovered from culture supernatants (FIGS. 4C and 4D). In contrast, for CHIKV-WT infected cells virus titres started to increase at 8 h post infection. Results suggest that, although synthesis of viral RNA in infected cells was not reduced, mutation of the capsid protein NoLS causes a defect in infectious virus particle formation causing reduction and delay of release of viral progeny. Together, these data suggests that subnuclear localisation of CHIKV capsid protein in not a hallmark of infection across different host cells and that the attenuation of CHIKV-NoLS in both mammalian and insect cells is likely the result of a defect in infectious virus particle formation due to the NoLS mutation.

Example 15—Multi Step Growth Kinetics of P5 CHIKV-NoLS

The CHIKV-NoLS vaccine candidate was passaged in Vero cells to assess phenotypic stability. T-75 flasks were grown to 90-95% confluency and infected at a multiplicity of infection (MOI) of 0.1 PFU/cell with CHIKV-NoLS or CHIKV-WT. Following 24 h of incubation at 37° C., culture media was used to infect another flask of Vero cells at MOI of 0.1. After 5 serial passages the growth kinetics of P5 CHIKV-NoLS was compared to CHIKV-WT and CHIKV-NoLS at passage 0 (P0).

C636 insect cells were infected at a multiplicity of infection (MOI) of 0.1 pfu/cell. Following adsorption of virus for 1 h at 37° C., cell monolayers were washed and fresh growth medium was added. Supernatants were collected at indicated time points and infectious virus quantified by plaque assay.

Figure 13:
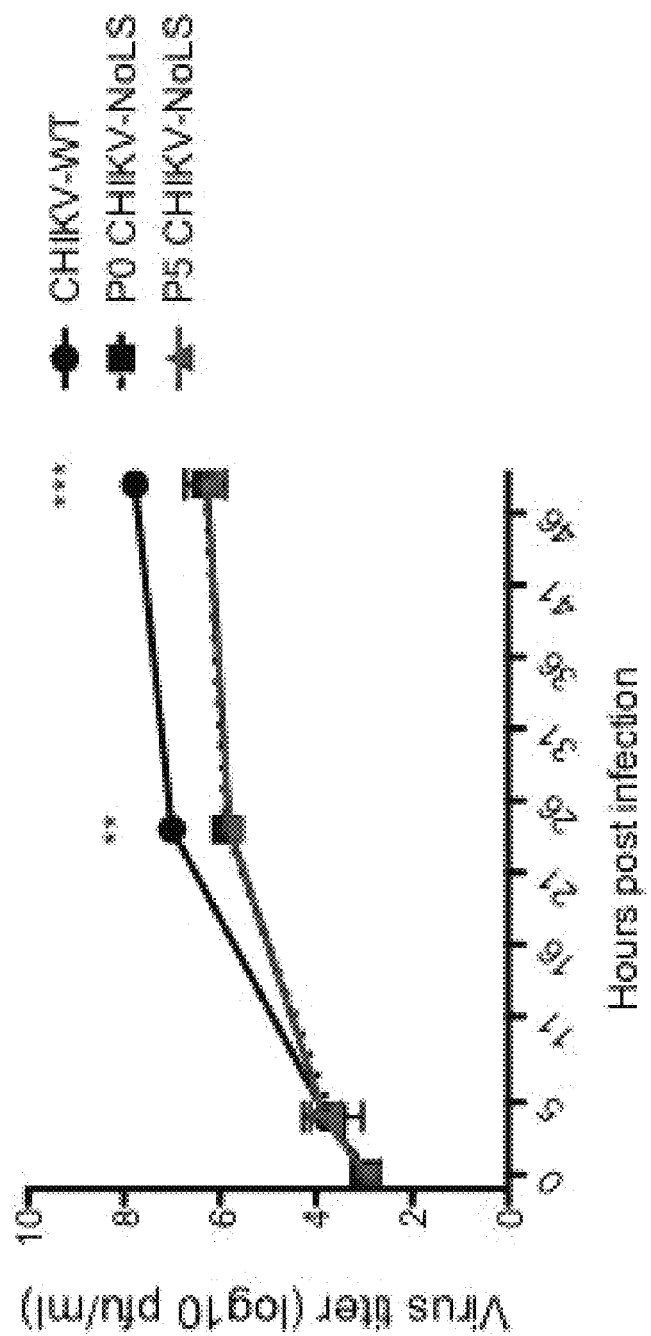
FIG. 13 Graph of virus titer versus hours post infection showing multistep growth kinetics of CHIKV-WT and CHIKV-NoLS in Vero cells to assess phenotypic stability. , $P<0.01$ and *, $P<0.001$ using two-way ANOVA with Bonferroni post-tests.

As seen in FIG. 13, P5 CHIKV-NoLS shows similar multi step replication kinetics to P0 CHIKV-NoLS. P0 CHIKV-NoLS and P5 CHIKV-NoLS show significantly reduced infectious titers at 24 and 48 hours post infection. This indicates that after 5 passages in Vero cells, replication of CHIKV-NoLS in insect cells remains significantly impaired compared to CHIKV-WT. The attenuated replication phenotype of CHIKV-NoLS remains stable after 5 passages in Vero cells.

Example 16—CHIKV NoLs Stability Following Cell Culture Passage—Plaque Size

Figure 14:
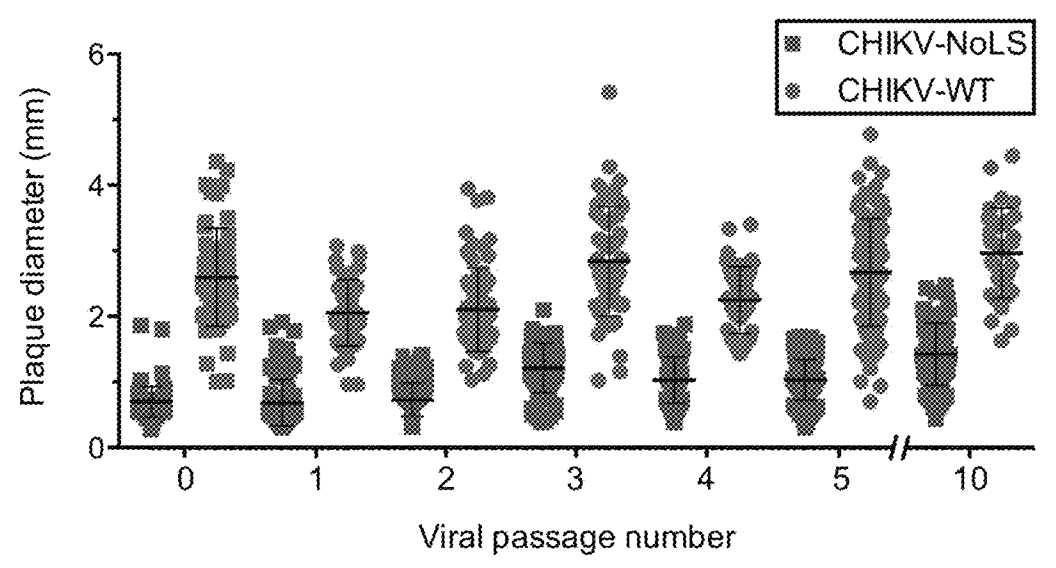

The CHIKV-NoLS vaccine candidate was passaged in Vero cells to assess phenotypic stability. T-75 flasks were grown to 90-95% confluency and infected at a multiplicity of infection (MOI) of 0.1 PFU/cell with CHIKV-NoLS or CHIKV-WT. Following 24 h of incubation at 37° C., culture media was used to infect another flask of Vero cells at MOI of 0.1. After 10 serial passages Vero plaque sizes were measured and compared to assess stability. Results are shown in FIG. 14.

CHIKV-NoLS has a small plaque phenotype in mammalian cells, indicating a reduced ability of the virus to spread from the initial site of infection and thus attenuation. To assess its phenotypic stability, CHIKV-NoLS was passaged 10 times in Vero cells at 37° C. using a multiplicity of infection of 0.1 PFU/cell.

The average plaque size of CHIKV-NoLS remained notably smaller than CHIKV-WT after 10 passages. CHIKV-NoLS also exhibited more homogeneous plaque morphology than CHIKV-WT. Results show that, after 10 passages, CHIKV-NoLS does not revert to a CHIKV-WT plaque phenotype and suggest that the CHIKV-NoLS vaccine candidate remains attenuated in its ability to spread from the initial site of infection.

Example 17—Effect of Filtration on CHIKV NoLs

This example shows that a viable live attenuated vaccine candidate can be produced in large quantities, with little loss of vaccine yield following filtration.

To examine the loss of CHIKV-NoLS yield during virus propagation filtration, the titer of CHIKV-NoLS before and after 0.22 μm filtration was measured. The results are shown in FIG. 15.

Average CHIKV-NoLS titers before and after filtration: Unfiltered—$1.57 \times 10^6$ PFU/ml; PVDF (hydrophilic PVDF membrane 0.22 μm pore size)—$1.09 \times 10^6$ PFU/ml; and PES (hydrophilic Polyethersulfone membrane 0.22 μm pore size)—$1.19 \times 10^6$ PFU/ml.

Example 18—Effect of Temperature on CHIKV NoLs During Long-Term Storage

This example shows that a viable live attenuated vaccine candidate can be stored long-term at either −20° C. or −80° C.

Although able to be stored stably at −80° C., storage of CHIKV-NoLS at −20° C. or 4° C. would reduce the cost of storing CHIKV-NoLS. Storage at −20° C., the temperature of a regular freezer, would also increase the accessibility of CHIKV-NoLS to wider populations.

The effect of temperature (21° C., 4° C., −20° C. and −80° C.) on long-term CHIKV-NoLS storage is shown in FIG. 16(A) and the effect of temperature (21° C., 4° C., −20° C. and −80° C.) on long-term CHIKV-WT storage is shown in FIG. 16(B).

No infectious CHIKV-NoLS or CHIKV-WT was detected after 28 days when stored at 21° C., room temperature. After 56 days at 4° C. the titer of CHIKV-NoLS fell to 110 pfu/ml and CHIKV-WT to 450 pfu/ml. The titer of CHIKV-NoLS and CHIKV-WT remained stable after 56 days when stored at either −20° C. or −80° C.

The above Examples demonstrate the following:

Mutating the NoLs of CHIKV capsid protein attenuates CHIKV replication in vitro.

Capsid-101/95 (CHIKV-NoLS) infected mice showed no disease signs, reduced viraemia and reduced expression of inflammatory mediators, making Capsid-101/95 (CHIKV-NoLS) an ideal live attenuated vaccine candidate.

Capsid-101/95 (CHIKV-NoLS) immunised mice are protected from disease when challenged with CHIKV wild-type capsid protein.

Capsid-101/95 (CHIKV-NoLS) immunised mice develop CHIKV specific neutralising antibodies.

Capsid-101/95 (CHIKV-NoLS) is likely to offer alphaviral cross protection, including viraemia upon Ross River virus challenge.

A viable live attenuated vaccine candidate can be produced in large quantities, with little loss of vaccine yield following filtration.

A viable live attenuated vaccine candidate can be stored long-term at either −20° C. or −80° C.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

The invention claimed is:

1. A vaccine selected from the group consisting of:
   (a) an isolated, purified, synthetic or recombinant Chikungunya virus (CHIKV) mutated capsid protein;
   (b) an isolated, purified, synthetic or recombinant CHIKV nascent structural polyprotein comprising a mutated CHIKV capsid protein;
   (c) a recombinant CHIKV genome encoding a mutated CHIKV capsid protein;
   (d) a recombinant CHIKV comprising a mutated CHIKV capsid protein;
   (e) a live attenuated recombinant CHIKV comprising a mutated CHIKV capsid protein;
   (f) a chimeric alphavirus comprising a mutated CHIKV capsid protein;
   (g) a live attenuated chimeric alphavirus comprising a mutated CHIKV capsid protein; and
   (h) an inactivated attenuated recombinant CHIKV comprising a mutated CHIKV capsid protein, wherein the mutated CHIKV capsid protein has at least a mutated nucleolar localization region (NoLS) compared with wildtype CHIKV capsid protein and is incapable or substantially incapable of nucleolar localization, and
   wherein:
   the mutated CHIKV capsid protein comprises at least amino acid positions 62, 63, 65, 66, 68, 69, 101 and 102 of wild-type CHIKV capsid protein shifted in position, replaced and/or deleted, and wherein the corresponding region of wild-type CHIKV capsid protein is shown in SEQ. ID NO. 3; or
   the mutated NoLS sequence is selected from the group consisting of SEQ. ID NO. 4, SEQ. ID NO. 5, SEQ. ID NO. 6 and SEQ. ID NO. 7.

2. The vaccine of claim 1, wherein the chimeric alphavirus of (f) and (g) is selected from the group consisting of Ross River virus (RRV), Barmah Forest virus (BFV), O'nyong-nyong virus (ONNV), Mayaro virus (MAYV), Sindbis virus group (causing Pogosta disease, Ockelbo disease and Karelian fever), and Semliki Forest virus (SFV).

3. The vaccine of claim 1, wherein the mutated CHIKV capsid protein comprises at least amino acid positions 62, 63, 65, 66, 68, 69, 101 and 102 of wild-type CHIKV capsid protein shifted in position, replaced and/or deleted, and wherein the corresponding region of wild-type CHIKV capsid protein is shown in SEQ. ID NO. 3.

4. The vaccine of claim 1, wherein the mutated NoLS sequence is selected from the group consisting of SEQ. ID NO. 4, SEQ. ID NO. 5, SEQ. ID NO. 6 and SEQ. ID NO. 7.

5. The vaccine of claim 4, wherein the mutated NoLS sequence comprises the sequence of SEQ. ID NO. 4.

6. The vaccine of claim 4, wherein the mutated NoLS sequence comprises the sequence of SEQ. ID NO. 5.

7. The vaccine of claim 4, wherein the mutated NoLS sequence comprises the sequence of SEQ. ID NO. 6.

8. The vaccine of claim 4, wherein the mutated NoLS sequence comprises the sequence of SEQ. ID NO. 7.

9. A vaccine or sub-unit vaccine selected from the group consisting of a recombinant CHIKV comprising a mutated CHIKV capsid protein, a recombinant CHIKV nascent structural polyprotein comprising a mutated CHIKV capsid protein, and a recombinant CHIKV genome encoding a mutated capsid protein, wherein the mutated CHIKV capsid protein is a nucleolar localization region (NoLS) mutant of wild-type CHIKV capsid protein incapable or substantially incapable of nucleolar localization, and wherein:

the mutated CHIKV capsid protein comprises at least amino acid positions 62, 63, 65, 66, 68, 69, 101 and 102 of wild-type CHIKV capsid protein shifted in position, replaced and/or deleted, and wherein the corresponding region of wild-type CHIKV capsid protein is shown in SEQ. ID NO. 3; or the mutated NoLS sequence is selected from the group consisting of SEQ. ID NO. 4, SEQ. ID NO. 5, SEQ. ID NO. 6 and SEQ. ID NO. 7.

* * * * *

SEQUENCE LISTING

<160> NUMBER OF SEQ ID NOS: 24

<210> SEQ ID NO 1
<211> LENGTH: 261
<212> TYPE: PRT
<213> ORGANISM: Chikungunya virus

<400> SEQUENCE: 1

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
                20                  25                  30

Arg Pro Gln Arg Gln Ala Gly Gln Leu Ala Gln Leu Ile Ser Ala Val
            35                  40                  45

Asn Lys Leu Thr Met Arg Ala Val Pro Gln Gln Lys Pro Arg Arg Asn
    50                  55                  60

Arg Lys Asn Lys Lys Gln Lys Gln Gln Ala Pro Gln Asn Asn
65                  70                  75                  80

Thr Asn Gln Lys Lys Gln Pro Pro Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

```
Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp
            260

<210> SEQ ID NO 2
<211> LENGTH: 267
<212> TYPE: PRT
<213> ORGANISM: Semliki Forest virus

<400> SEQUENCE: 2

Met Asn Tyr Ile Pro Thr Gln Thr Phe Tyr Gly Arg Arg Trp Arg Pro
1               5                   10                  15

Arg Pro Ala Ala Arg Pro Trp Pro Leu Gln Ala Thr Pro Val Ala Pro
            20                  25                  30

Val Val Pro Asp Phe Gln Ala Gln Gln Met Gln Gln Leu Ile Ser Ala
        35                  40                  45

Val Asn Ala Leu Thr Met Arg Gln Asn Ala Ile Ala Pro Ala Arg Pro
50                  55                  60

Pro Lys Pro Lys Lys Lys Thr Thr Lys Pro Lys Pro Lys Thr Gln
65                  70                  75                  80

Pro Lys Lys Ile Asn Gly Lys Thr Gln Gln Lys Lys Lys Asp Lys
                85                  90                  95

Gln Ala Asp Lys Lys Lys Lys Pro Gly Lys Arg Glu Arg Met Cys
            100                 105                 110

Met Lys Ile Glu Asn Asp Cys Ile Phe Glu Val Lys His Glu Gly Lys
            115                 120                 125

Val Thr Gly Tyr Ala Cys Leu Val Gly Asp Lys Val Met Lys Pro Ala
            130                 135                 140

His Val Lys Gly Val Ile Asp Asn Ala Asp Leu Ala Lys Leu Ala Phe
145                 150                 155                 160

Lys Lys Ser Ser Lys Tyr Asp Leu Glu Cys Ala Gln Ile Pro Val His
                165                 170                 175

Met Arg Ser Asp Ala Ser Lys Tyr Thr His Glu Lys Pro Glu Gly His
            180                 185                 190

Tyr Asn Trp His His Gly Ala Val Gln Tyr Ser Gly Gly Arg Phe Thr
            195                 200                 205

Ile Pro Thr Gly Ala Gly Lys Pro Gly Asp Ser Gly Arg Pro Ile Phe
            210                 215                 220

Asp Asn Lys Gly Arg Val Val Ala Ile Val Leu Gly Gly Ala Asn Glu
225                 230                 235                 240

Gly Ser Arg Thr Ala Leu Ser Val Val Thr Trp Asn Lys Asp Met Val
                245                 250                 255

Thr Arg Val Thr Pro Glu Gly Ser Glu Glu Trp
            260                 265

<210> SEQ ID NO 3
<211> LENGTH: 53
<212> TYPE: PRT
<213> ORGANISM: Chikungunya virus

<400> SEQUENCE: 3

Gln Gln Lys Pro Arg Arg Asn Arg Lys Asn Lys Lys Gln Lys Gln
1               5                   10                  15
```

Gln Gln Ala Pro Gln Asn Asn Thr Asn Gln Lys Lys Gln Pro Pro Lys
            20                  25                  30

Lys Lys Pro Ala Gln Lys Lys Lys Pro Gly Arg Arg Glu Arg Met
        35                  40                  45

Cys Met Lys Ile Glu
        50

<210> SEQ ID NO 4
<211> LENGTH: 53
<212> TYPE: PRT
<213> ORGANISM: Chikungunya virus

<400> SEQUENCE: 4

Gln Gln Lys Pro Ala Ala Asn Ala Ala Asn Ala Ala Gln Lys Gln Lys
1               5                   10                  15

Gln Gln Ala Pro Gln Asn Asn Thr Asn Gln Lys Lys Gln Pro Pro Lys
            20                  25                  30

Lys Lys Pro Ala Gln Lys Lys Lys Pro Gly Arg Arg Glu Arg Met
        35                  40                  45

Cys Met Lys Ile Glu
        50

<210> SEQ ID NO 5
<211> LENGTH: 53
<212> TYPE: PRT
<213> ORGANISM: Chikungunya virus

<400> SEQUENCE: 5

Gln Gln Lys Pro Arg Arg Asn Arg Lys Asn Lys Lys Gln Lys Gln Lys
1               5                   10                  15

Gln Gln Ala Pro Gln Asn Asn Thr Asn Gln Ala Ala Gln Pro Pro Lys
            20                  25                  30

Lys Lys Pro Ala Gln Ala Ala Lys Pro Gly Ala Ala Glu Arg Met
        35                  40                  45

Cys Met Lys Ile Glu
        50

<210> SEQ ID NO 6
<211> LENGTH: 53
<212> TYPE: PRT
<213> ORGANISM: Chikungunya virus

<400> SEQUENCE: 6

Gln Gln Lys Pro Ala Ala Asn Ala Ala Asn Ala Ala Gln Lys Gln Lys
1               5                   10                  15

Gln Gln Ala Pro Gln Asn Asn Thr Asn Gln Lys Lys Gln Pro Pro Lys
            20                  25                  30

Lys Lys Pro Ala Gln Lys Lys Lys Pro Gly Ala Ala Glu Arg Met
        35                  40                  45

Cys Met Lys Ile Glu
        50

<210> SEQ ID NO 7
<211> LENGTH: 53
<212> TYPE: PRT
<213> ORGANISM: Chikungunya virus

<400> SEQUENCE: 7

Gln Gln Lys Pro Ala Ala Asn Ala Ala Asn Ala Ala Gln Lys Gln Lys
1               5                   10                  15

-continued

```
Gln Gln Ala Pro Gln Asn Asn Thr Asn Gln Lys Lys Gln Pro Pro Lys
            20                  25                  30

Lys Lys Pro Ala Gln Ala Ala Lys Lys Pro Gly Ala Ala Glu Arg Met
        35                  40                  45

Cys Met Lys Ile Glu
    50

<210> SEQ ID NO 8
<211> LENGTH: 32
<212> TYPE: DNA
<213> ORGANISM: Artificial Sequence
<220> FEATURE:
<223> OTHER INFORMATION: Oligonucleotide

<400> SEQUENCE: 8
gcggcgcaag cttatggagt tcatcccaac cc                                    32

<210> SEQ ID NO 9
<211> LENGTH: 27
<212> TYPE: DNA
<213> ORGANISM: Artificial Sequence
<220> FEATURE:
<223> OTHER INFORMATION: Based on CHIKV Capsid Protein sequence

<400> SEQUENCE: 9
cgcggatccg actcttcggc cccctcg                                          27

<210> SEQ ID NO 10
<211> LENGTH: 24
<212> TYPE: DNA
<213> ORGANISM: Artificial Sequence
<220> FEATURE:
<223> OTHER INFORMATION: Based on CHIKV Capsid Protein sequence

<400> SEQUENCE: 10
cgcggatccg accactcttc ggcc                                             24

<210> SEQ ID NO 11
<211> LENGTH: 43
<212> TYPE: DNA
<213> ORGANISM: Artificial Sequence
<220> FEATURE:
<223> OTHER INFORMATION: Oligonucleotide

<400> SEQUENCE: 11
caaaacaaca caaatcaagc ggcgcagcca cctaaaaaga aac                        43

<210> SEQ ID NO 12
<211> LENGTH: 43
<212> TYPE: DNA
<213> ORGANISM: Artificial Sequence
<220> FEATURE:
<223> OTHER INFORMATION: Oligonucleotide

<400> SEQUENCE: 12
gttttgttgt gtttagttcg ccgcgtcggt ggatttttct ttg                        43

<210> SEQ ID NO 13
<211> LENGTH: 31
<212> TYPE: DNA
<213> ORGANISM: Artificial Sequence
<220> FEATURE:
<223> OTHER INFORMATION: Oligonucleotide

<400> SEQUENCE: 13
```

```
gaaaccggct caagcggcaa agaagccggg c                                     31
```

<210> SEQ ID NO 14
<211> LENGTH: 31
<212> TYPE: DNA
<213> ORGANISM: Artificial Sequence
<220> FEATURE:
<223> OTHER INFORMATION: Oligonucleotide

<400> SEQUENCE: 14

```
ctttggccga gttcgccgtt tcttcggccc g                                     31
```

<210> SEQ ID NO 15
<211> LENGTH: 38
<212> TYPE: DNA
<213> ORGANISM: Artificial Sequence
<220> FEATURE:
<223> OTHER INFORMATION: Oligonucleotide

<400> SEQUENCE: 15

```
gaagccgggc gccgcagaga ggatgtgcat gaaaatcg                              38
```

<210> SEQ ID NO 16
<211> LENGTH: 38
<212> TYPE: DNA
<213> ORGANISM: Artificial Sequence
<220> FEATURE:
<223> OTHER INFORMATION: Oligonucleotide

<400> SEQUENCE: 16

```
cttcggcccg cggcgtctct cctacacgta cttttagc                              38
```

<210> SEQ ID NO 17
<211> LENGTH: 42
<212> TYPE: DNA
<213> ORGANISM: Artificial Sequence
<220> FEATURE:
<223> OTHER INFORMATION: Oligonucleotide

<400> SEQUENCE: 17

```
gcggtacccc aacagaagcc agccgcgaat cggaagaata ag                         42
```

<210> SEQ ID NO 18
<211> LENGTH: 42
<212> TYPE: DNA
<213> ORGANISM: Artificial Sequence
<220> FEATURE:
<223> OTHER INFORMATION: Oligonucleotide

<400> SEQUENCE: 18

```
cgccatgggg ttgtcttcgg tcggcgctta gccttcttat tc                         42
```

<210> SEQ ID NO 19
<211> LENGTH: 42
<212> TYPE: DNA
<213> ORGANISM: Artificial Sequence
<220> FEATURE:
<223> OTHER INFORMATION: Oligonucleotide

<400> SEQUENCE: 19

```
gaatcggaag aatgcggcgc aaaagcaaaa acaacaggcg cc                         42
```

<210> SEQ ID NO 20
<211> LENGTH: 42
<212> TYPE: DNA

```
<213> ORGANISM: Artificial Sequence
<220> FEATURE:
<223> OTHER INFORMATION: Oligonucleotide

<400> SEQUENCE: 20
cttagccttc ttacgccgcg ttttcgtttt tgttgtccgc gg                    42

<210> SEQ ID NO 21
<211> LENGTH: 32
<212> TYPE: DNA
<213> ORGANISM: Artificial Sequence
<220> FEATURE:
<223> OTHER INFORMATION: Oligonucleotide

<400> SEQUENCE: 21
cagccgcgaa tgcggcgaat gcggcgcaaa ag                              32

<210> SEQ ID NO 22
<211> LENGTH: 32
<212> TYPE: DNA
<213> ORGANISM: Artificial Sequence
<220> FEATURE:
<223> OTHER INFORMATION: Oligonucleotide

<400> SEQUENCE: 22
gtcggcgctt acgccgctta cgccgcgttt tc                              32

<210> SEQ ID NO 23
<211> LENGTH: 18
<212> TYPE: DNA
<213> ORGANISM: Artificial Sequence
<220> FEATURE:
<223> OTHER INFORMATION: Oligonucleotide

<400> SEQUENCE: 23
cccggtaaga gcggtgaa                                              18

<210> SEQ ID NO 24
<211> LENGTH: 17
<212> TYPE: DNA
<213> ORGANISM: Artificial Sequence
<220> FEATURE:
<223> OTHER INFORMATION: Oligonucleotide

<400> SEQUENCE: 24
cttccggtat gtcgatg                                               17
```